(12) United States Patent
Wellenstein

(10) Patent No.: US 10,881,293 B2
(45) Date of Patent: Jan. 5, 2021

(54) SYSTEMS AND METHODS FOR SURVEYING THE SCLERA OF THE EYE

(71) Applicant: BRANDEIS UNIVERSITY, Waltham, MA (US)

(72) Inventor: Hermann Wellenstein, Waltham, MA (US)

(73) Assignee: Brandeis University, Waltham, MA (US)

( * ) Notice: Subject to any disclaimer, the term of this patent is extended or adjusted under 35 U.S.C. 154(b) by 89 days.

(21) Appl. No.: 16/318,910

(22) PCT Filed: Jul. 21, 2017

(86) PCT No.: PCT/US2017/043324
§ 371 (c)(1),
(2) Date: Jan. 18, 2019

(87) PCT Pub. No.: WO2018/017972
PCT Pub. Date: Jan. 25, 2018

(65) Prior Publication Data
US 2019/0216315 A1 Jul. 18, 2019

Related U.S. Application Data

(60) Provisional application No. 62/365,660, filed on Jul. 22, 2016.

(51) Int. Cl.
*A61B 3/10* (2006.01)
*A61B 3/107* (2006.01)
(Continued)

(52) U.S. Cl.
CPC ............ *A61B 3/107* (2013.01); *A61B 3/0025* (2013.01); *A61B 3/14* (2013.01); *A61B 3/0008* (2013.01)

(58) Field of Classification Search
CPC ......... A61B 3/113; A61B 3/14; A61B 3/0008; A61B 3/102; A61B 3/10; A61B 3/12; A61B 3/13; A61B 3/107
(Continued)

(56) References Cited

U.S. PATENT DOCUMENTS 8,118,752 B2  2/2012 Hetling et al.
8,388,134 B2  3/2013 Goldstein
(Continued)

OTHER PUBLICATIONS

International Search Report and Written Opinion for International Patent Application No. PCT/US2017/043324 dated Jul. 21, 2017.
(Continued)

*Primary Examiner* — Hung X Dang
(74) *Attorney, Agent, or Firm* — Quarles & Brady LLP

(57) ABSTRACT

Systems and methods for surveying the sclera are provided. In some aspects, a method for generating a design for a prosthetic lens for an eye of a subject includes arranging an eye of a subject at a distance from a plurality of illumination sources and a plurality of imaging devices, projecting light onto the eye of the subject using the illumination sources, acquiring image data of the eye of the subject and the light using the plurality of imaging devices, generating a three dimensional map of the eye, including the sclera, using the image data; and designing, using the three dimensional map of the eye for the lens that fits over a cornea of the eye to engage the sclera and form a fluid pocket between the prosthetic lens that surrounds the cornea.

20 Claims, 19 Drawing Sheets

(51) Int. Cl.
*A61B 3/00* (2006.01)
*A61B 3/14* (2006.01)

(58) Field of Classification Search
USPC .................. 351/212, 221, 206, 205, 246
See application file for complete search history.

(56) References Cited

U.S. PATENT DOCUMENTS

| | | | |
|---|---|---|---|
| 9,295,388 | B2 | 3/2016 | Lawson |
| 9,398,845 | B2 | 7/2016 | Bishop |
| 2010/0328444 | A1 | 12/2010 | Blixt et al. |
| 2012/0163678 | A1 | 6/2012 | Du |
| 2014/0361984 | A1 | 12/2014 | Kim |
| 2015/0029463 | A1 | 1/2015 | Hetling et al. |
| 2015/0131055 | A1 | 5/2015 | Catanzariti |
| 2015/0138505 | A1* | 5/2015 | Grenon ............ A61B 3/0008 351/206 |

OTHER PUBLICATIONS

Vorotec. Scanner for Corneal Mapping. 2011. [Retrieved Sep. 14, 2017]. Retrieved from internet<:http://vorotec.eu/Scanner_for_comeal_mapping.html>, pp. 3-9.

Van Der Worp, E. A Guide to Sciera Lens Fitting. Pacific University. 2010. [Retrieved Sep. 11, 2017]. Retrieved from internet<http://commons.pacificu.edu/cgi/viewcontent.cgi?article=1003&context=mono> entire document.

Morrison, S. The Importance of Scleral Shape. Jun. 1, 2016. Contact Lens Spectrum. (Retrieved Sep. 14, 2017]. Retrieved from internet: <https://www.clspectrum.com/issues/2016/june-2016/the-importance-of-sclera I-shape> entire document.

Chennamma, HR et al, "A Survey on Eye-Gaze Tracking Techniques," Indian Journal of Computer Science and Engineering, ISSN : 0976-5166, vol. 4, No. 5, Oct.-Nov. 2013, pp. 388-393.

Visionary Optics, Brochure for sMap 3D, version L91 v2.0. Accessed Jul. 9, 2017.

Yoo, D. H. et al, "Non-contact eye gaze tracking system by mapping of corneal reflections," Automatic Face and Gesture Recognition, 2002. Proceedings. Fifth IEEE International Conference on, Washington, DC, 2002, pp. 94-99.

* cited by examiner

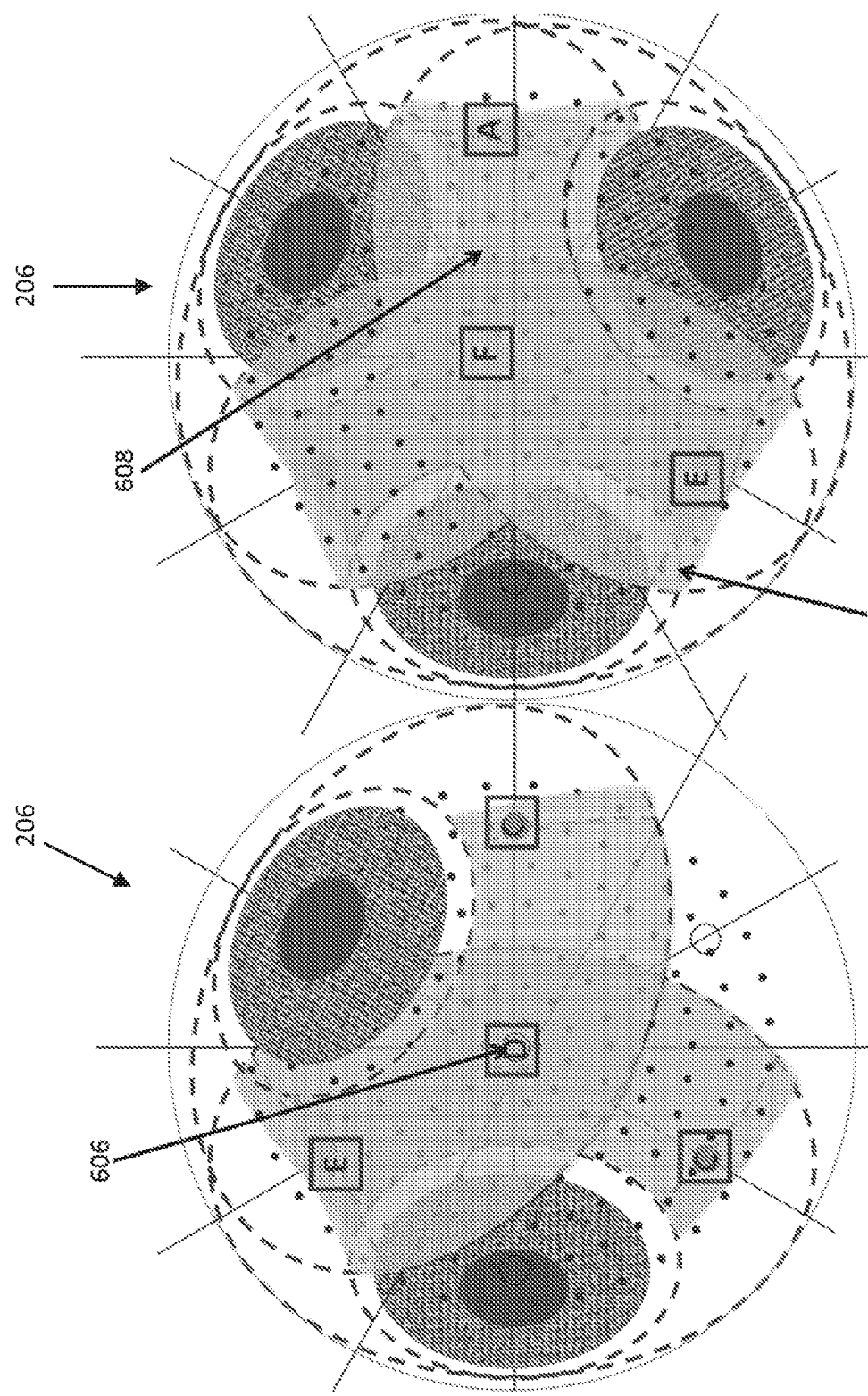

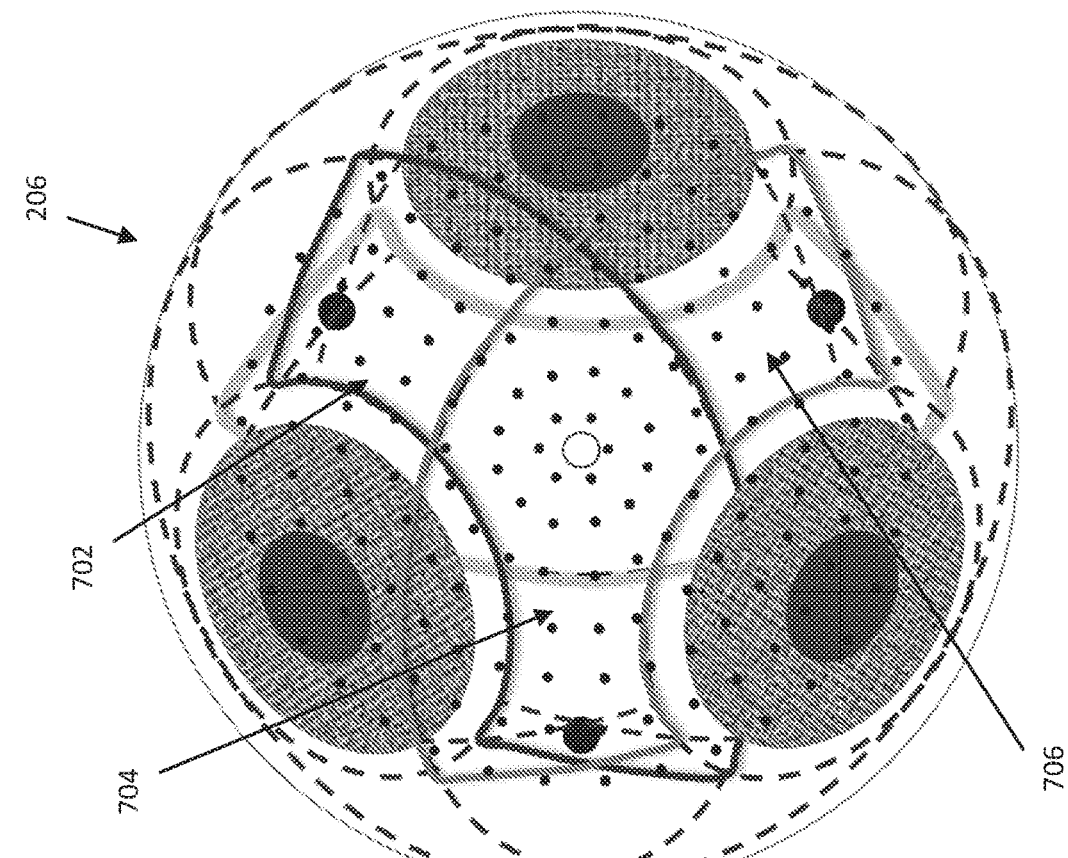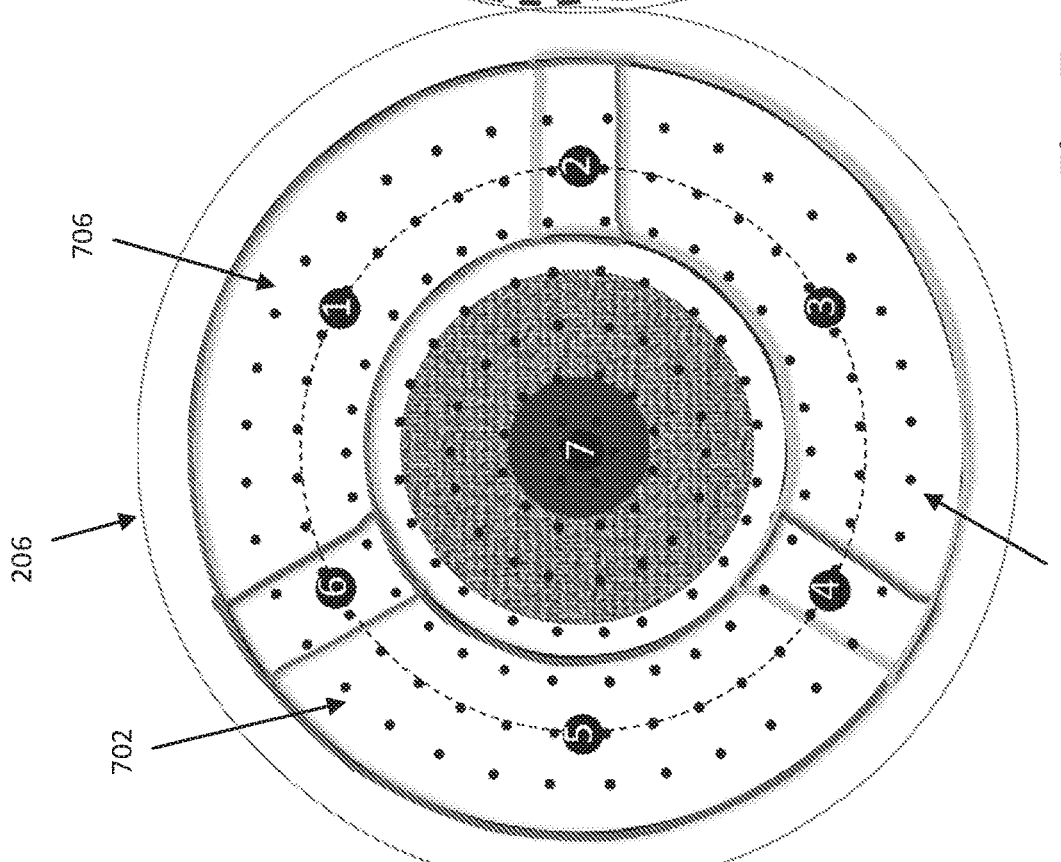
Fig. 7

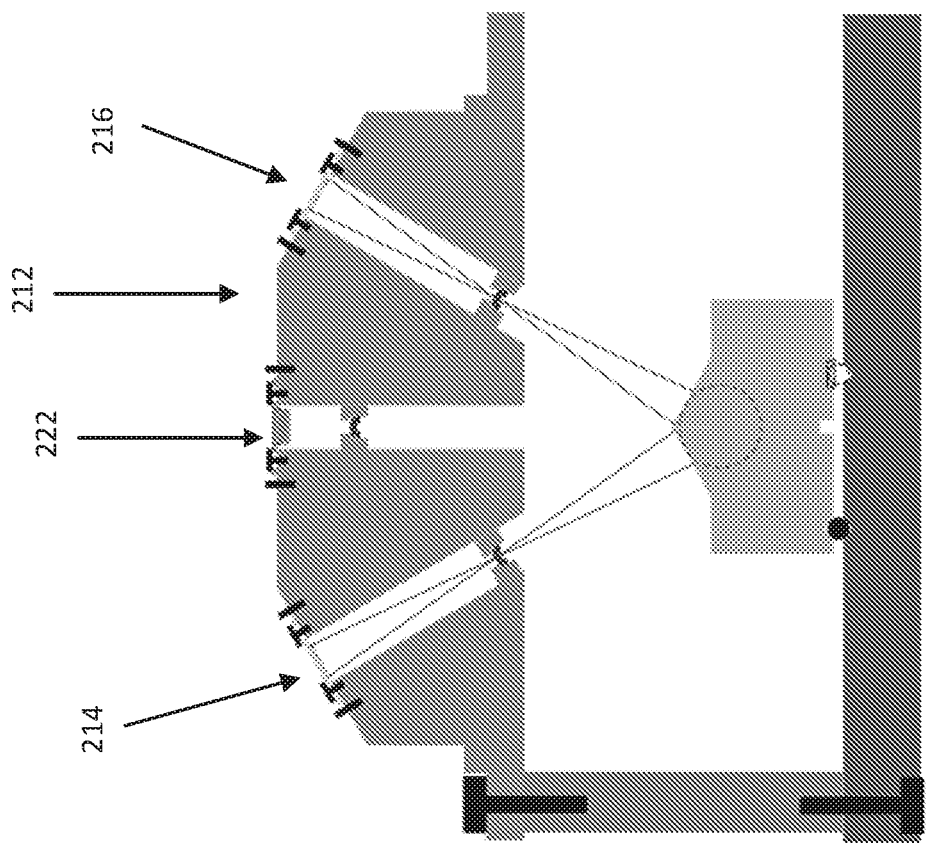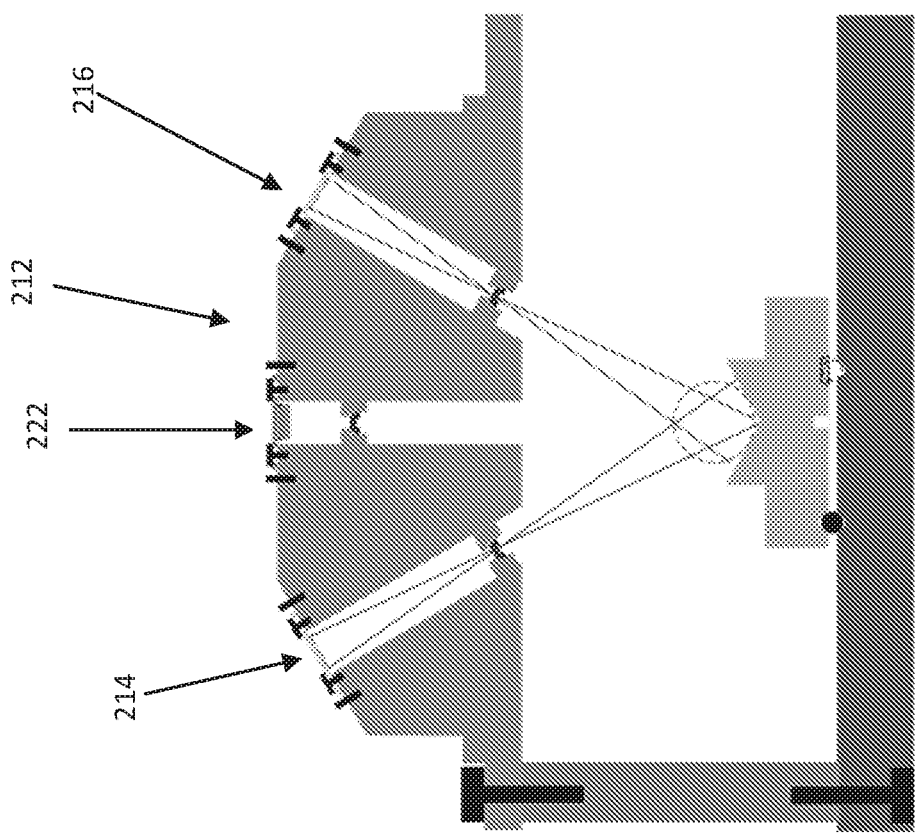
Fig. 15

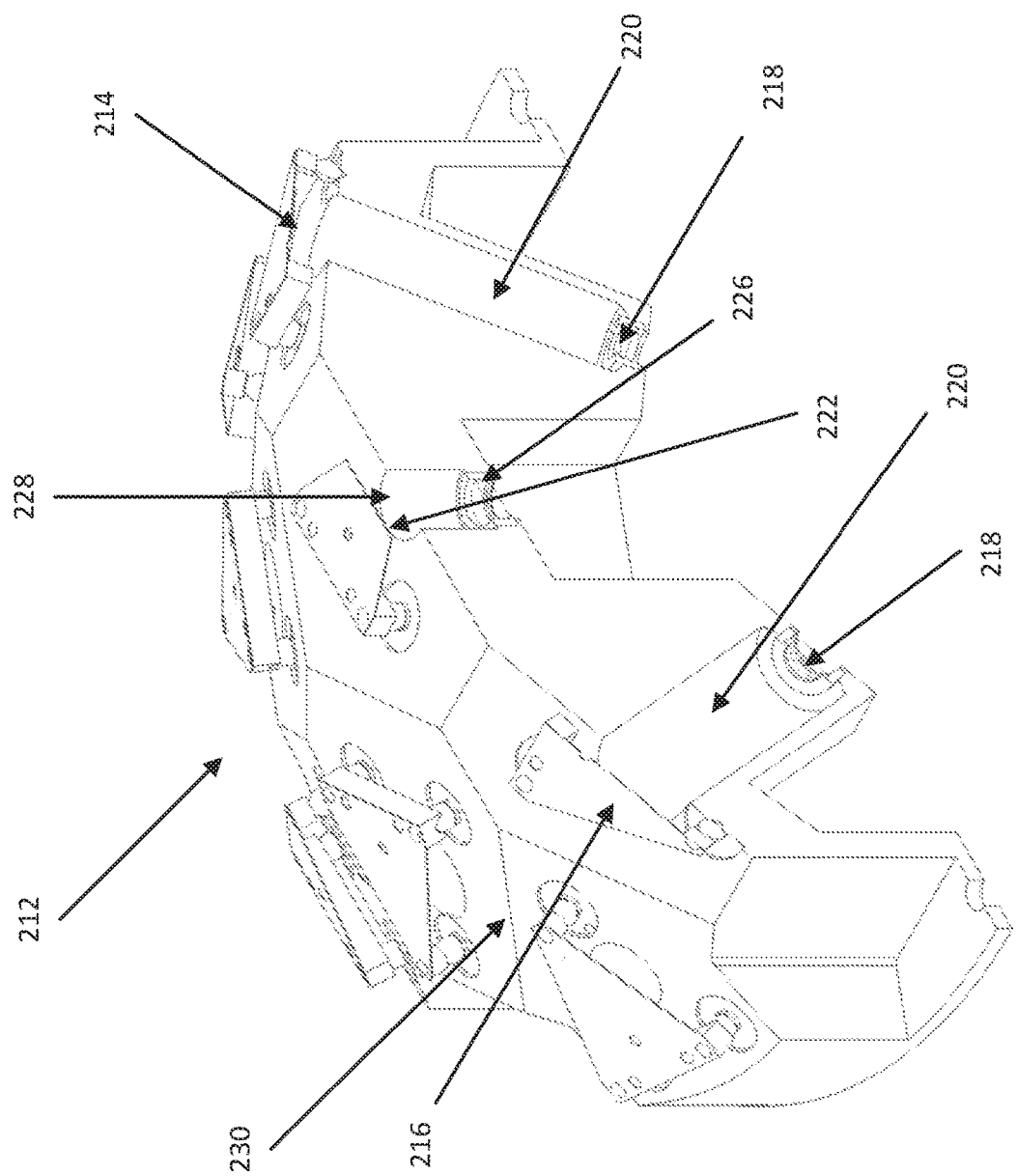

SYSTEMS AND METHODS FOR SURVEYING THE SCLERA OF THE EYE

CROSS-REFERENCE TO RELATED APPLICATIONS

The present application represents the U.S. National Stage of International Application No. PCT/US2017/043324, filed Jul. 21, 2017, which is based on, and incorporates herein, it its entirety, U.S. Provisional Patent Application No. 62/365,660 filed on Jul. 22, 2016.

STATEMENT REGARDING FEDERALLY SPONSORED RESEARCH

Background

The field of the disclosure relates to systems and methods for three-dimensional imaging. More particularly, the disclosure relates to systems and methods for surveying the eye.

Many people suffer from complex corneal diseases that cause severely impaired vision or even blindness. Extreme dryness of the eyes can lead to these problems as well. The vision of many of these patients cannot be corrected with typical glasses or contact lenses, as the shape of the cornea is no longer a smooth surface. Ophthalmologists have developed a scleral lens that restores the vision of patients with complex corneal problems due to disease or severe dryness. To create such a scleral lens, a large prosthetic device 20 is custom fabricated to fit onto the eyeball and restore vision. FIG. 1 shows a prosthetic lens 20 that is fitted with the eyeball such that a liquid reservoir 22 of saline solution is maintained between this lens 20 and the eye-ball to eliminate the cornea 24 as a refractive surface and, at the same time, keep the eye well lubricated. The process of fitting is done by trial and error where the lens 20, only a few millimeters (mm) less than the eye diameter, is fitted to seal onto the sclera 26. The seal is checked by inspection and, if necessary, a new lens is fabricated. This procedure may require three or more iterations before the lens fits properly.

Therefore, it would be desirable to have systems and methods to improve the efficiency of the fabrication and fitting process of such lenses, for example, by reducing the reliance on trial and error, so the sealing contour of the lens is more effective and efficient.

SUMMARY

The present disclosure provides systems and methods for surveying an eye to generate a three-dimensional map of the eye and/or sclera which can be used to facilitate, for example, the fabrication and/or fitting of a lens. In particular, the map of the surface of the sclera can be used to improve the sealing contour of the lens to make a substantially improved fabrication and fitting.

In accordance with one aspect of the disclosure, a system for mapping an exterior surface of an eye of a subject is provided. The system may include a support structure configured to engage the subject and position an eye of the subject in a predetermined position, one or more illumination sources configured to direct light spots on to the eye of the subject in the predetermined position, a plurality of imaging devices separated from and directed toward the support structure to acquire image data of the eye of the subject when the lights are positioned thereon, and a processor configured to receive the image data of the eye of the subject from the plurality of imaging devices and generate a three-dimensional map of the eye, including the sclera, from the image data.

In accordance with another aspect of the disclosure, a method for generating a prosthetic lens for an eye of a subject is provided. The method may include arranging an eye of a subject at a distance from a plurality of illumination sources and a plurality of imaging devices, projecting light spots onto the eye of the subject using the one or more illumination sources, acquiring image data of the eye of the subject using the plurality of imaging devices, generating a three-dimensional map of the eye, including the sclera, using the image data, and designing, using the three-dimensional map of the eye, a prosthetic lens that fits over a cornea of the eye to engage the sclera and form a fluid pocket between the prosthetic lens that surrounds the cornea.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 6B is a schematic illustration of an eye in two positions showing illuminations, markers, and fields of view of imaging devices relative to swaths in accordance with the present disclosure.

FIG. 6C is a schematic illustration of an eye in three positions showing illuminations, markers, and fields of view of imaging devices relative to swaths in accordance with the present disclosure.

FIG. 7 is another schematic illustration of an eye illustrating the use of additional swaths in accordance with further aspects of the present disclosure.

FIG. 15 shows the calibration of the projectors where the spots are projected onto two calibrated planes at different distances from the projectors.

FIG. 18 is a perspective view of the imaging unit body of FIG. 17B with a section removed to show the internal structure of the unit.

Figure 1:
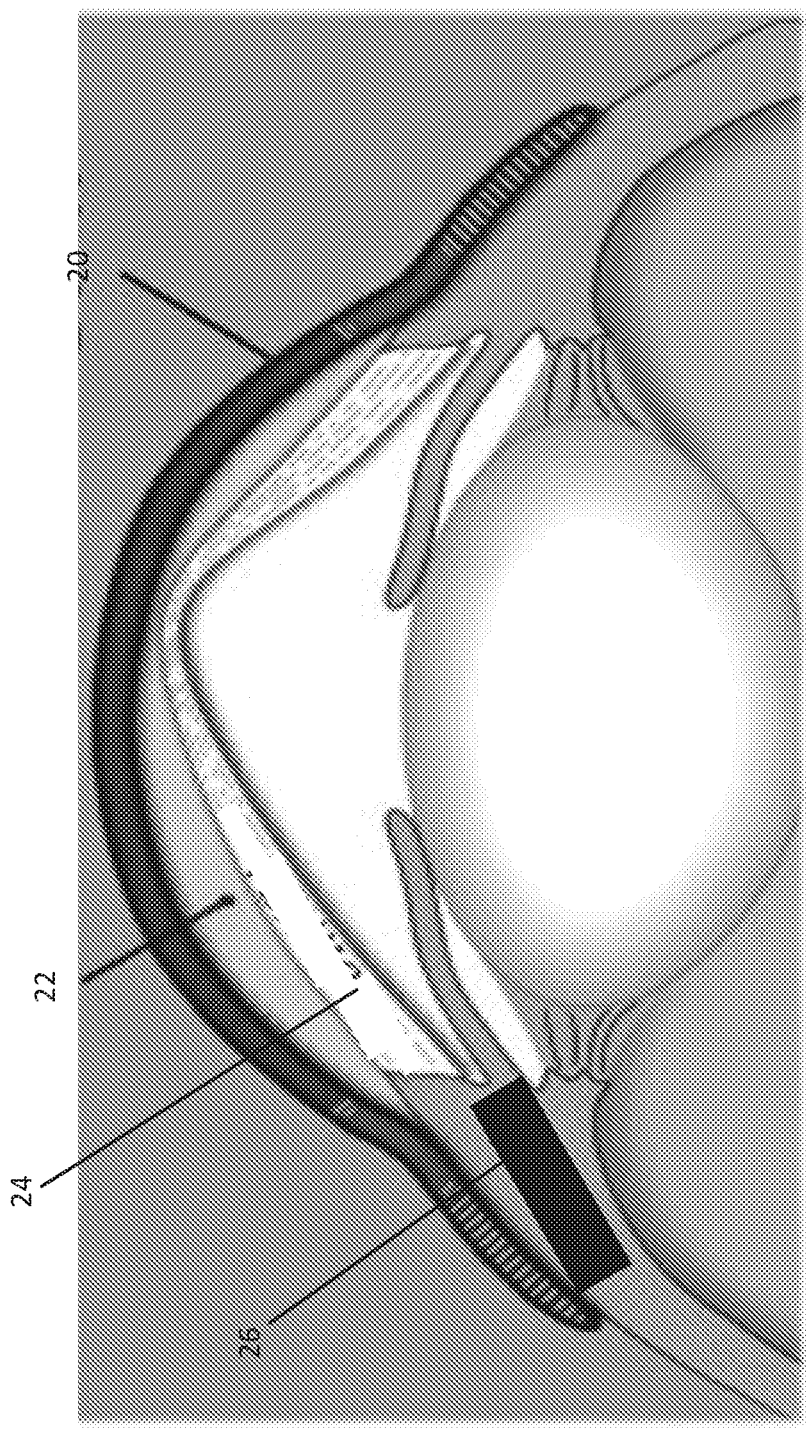
FIG. 1 is a schematic cross-sectional view of a prior art prosthetic lens that is fitted with an eyeball.

Corresponding reference characters indicate corresponding parts throughout the several views. Although the drawings represent embodiments of the present disclosure, the drawings are not necessarily to scale and certain features may be exaggerated in order to better illustrate and explain the embodiments of the present disclosure.

DETAILED DESCRIPTION OF THE INVENTION

Complex corneal diseases may cause severely impaired vision or even blindness. Extreme dryness of the eyes may also lead to these problems. The vision of these patients cannot be corrected with typical glasses or contact lenses, as the shape of the cornea is no longer a smooth surface.

Methods are developed to restore vision to such patients. For example, PROSE (Prosthetic Replacement of the Ocular Surface Ecosystem) requires custom fitted lenses that form a seal on the sclera, which allows a saline solution to be held between the prosthetic lens and the damaged tissue. This process creates a "new cornea" and thus restores vision. However, the lens fitting process is done entirely by trial and error in multiple lens-fitting sessions over several days. This iterative approach may cause patient discomfort while simultaneously increasing the time and cost of the overall process, making PROSE less appealing and accessible to those in need.

As such, a system and a method for surveying the eye and, more particularly, the sclera of the eye is needed. The disclosed systems and methods facilitate surveying, profiling, or mapping the eye (particularly the sclera) without making contact with the eye. As used herein, such systems may be referred to as a "Sclervey" or Sclervey system. The systems and methods described herein may generate a high-precision map of the eye and sclera non-invasively in a matter of minutes, providing medical professionals with the necessary data to efficiently design custom fitted lenses.

Figure 2:
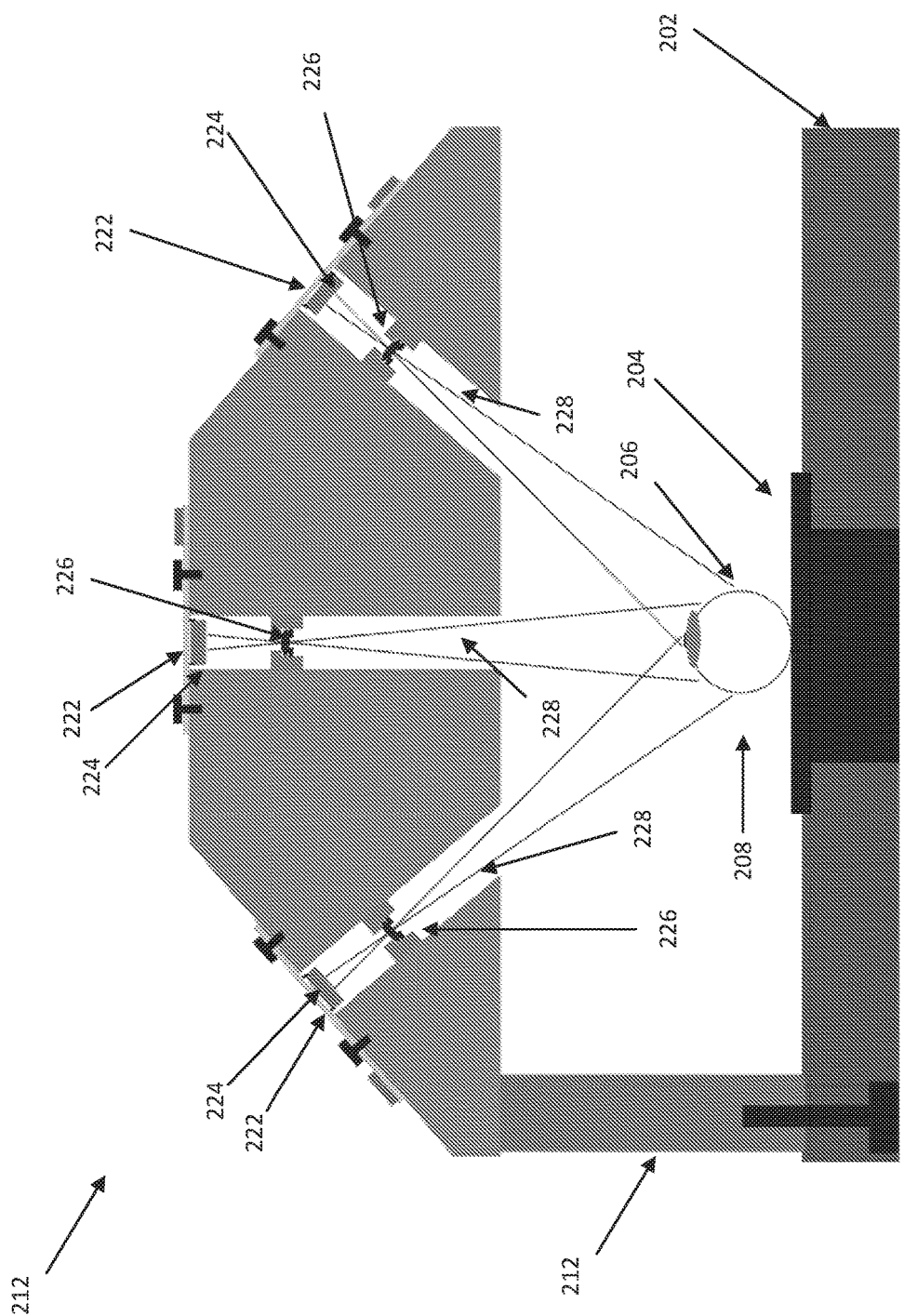
FIG. 2 is a schematic cross-sectional view of a system for mapping an eye in accordance with the present disclosure.
Figure 3:
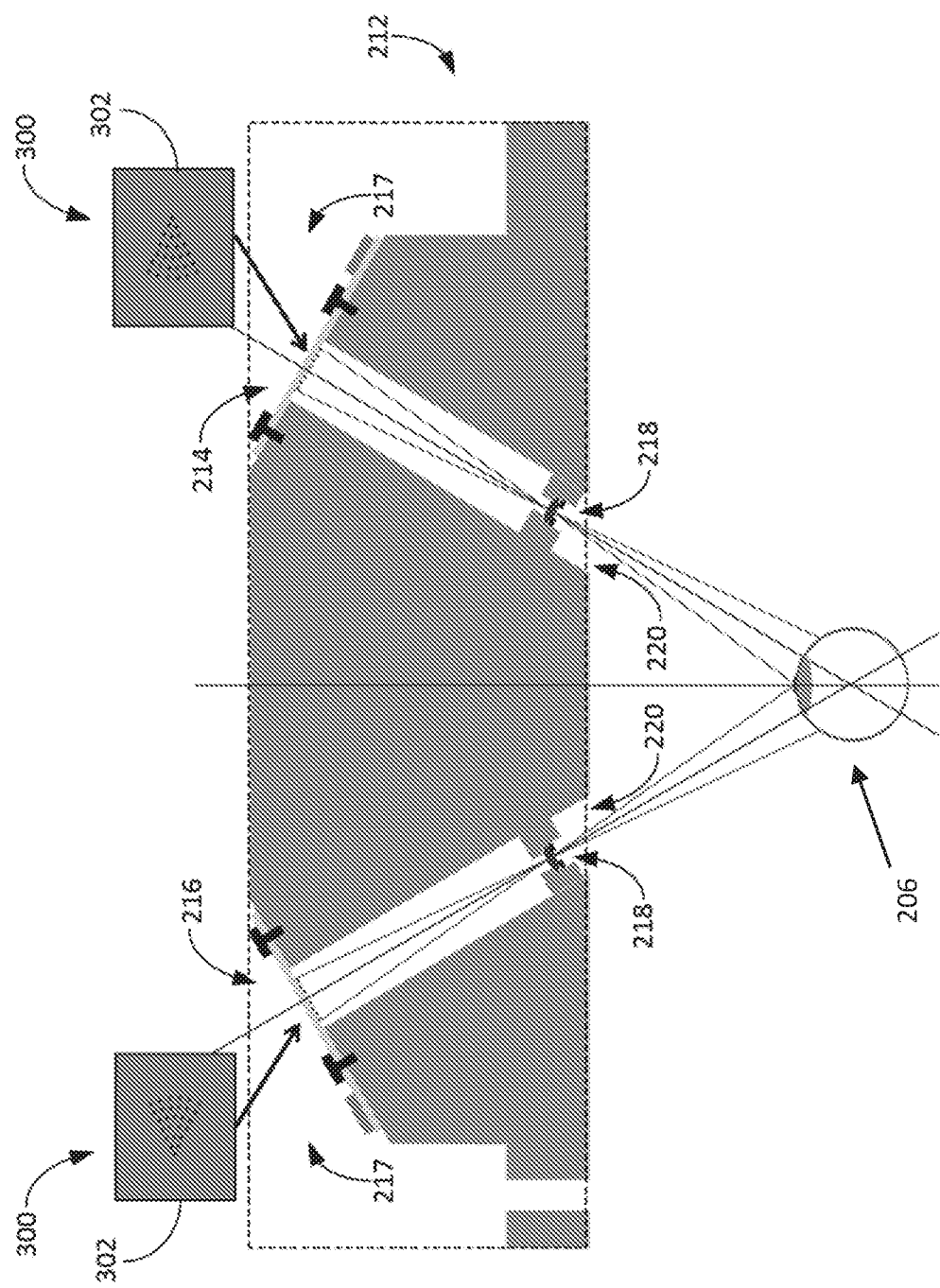
FIG. 3 is a schematic illustration of a distribution of the illumination sources of the imaging unit in the system of FIG. 2.

Specifically, referring now to FIGS. 2 and 3, a system 200 is illustrated for analyzing an eye and, in particular, a sclera, of a subject. The system 200 includes a support structure 202, which can accommodate the calibration process discussed below. The support structure 202 includes a patient-engagement frame 204 that is configured to engage a subject to position an eye 206 of the subject in a predetermined position 208. The support structure 202 extends from the patient-engagement frame 204, along a chassis 210 that couples the patient-engagement frame 204 to an imaging unit 212, such as a camera, for example. Thus, the eye 206 of the subject is arranged by the patient-engagement frame 204 in the predetermined position 208 opposite the imaging unit 212.

The imaging unit 212 may optionally include multiple illumination devices 214, 216, secured therein. The illumination devices 214, 216, as will be described may include a number of different illumination devices 214, 216, such as projectors and the like. Also, the illumination devices 214, 216 may be each formed from an assembly of components. In one non-limiting example, an illumination device 214, 216 may include a lighting source 217 and a focusing assembly 218 arranged along a light passage 220 extending through the imaging unit 212 to illuminate the eye 206 when arranged in the predetermined position.

The imaging unit 212 may also include multiple imaging devices, of which one example imaging device 222 is illustrated in FIG. 2. As will be described, it is contemplated that the imaging unit 212 will include at least two imaging devices, or is designed to acquire images or imaging data from two distinct positions relative to the eye 206 when arranged in the predetermined position. A given imaging device 222 may include an image capture component 224 and optional optics 226 arranged within an imaging passage 228 to acquire images or image data from the eye 206 when arranged in the predetermined position 208 opposite the imaging unit 212.

The illumination provided by the illumination devices 214, 216 may be designed to perform general illumination of the eye 206 to facilitate imaging by the imaging unit 212. That is, the illumination may be designed to achieve a general illumination dispersed across the eye 206, such that anatomical markers, such as blood vessels, can be identified in the images or imaging data, in addition to discerning a perimeter or surface of the eye 206. Additionally or alternatively, the illumination devices 214, 216 may be designed to create artificial markers, such as light spots, to substitute for or supplement the use of anatomical markers.

For example, in one particular implementation, systems and methods described herein may utilize both hardware and software designed for data acquisition to capture and process images. As will be described, systems and methods are provided that use markers, which may include anatomical markers, such as blood vessels, and/or artificial markers, such as light spots, to create a map of the eye. Data may be collected, for example, by taking stereo images of anatomical markers like blood vessels and/or focused LED light spots, which may be projected onto an eyeball. By using stereo reconstruction to compute the three-dimensional (3D) positions of the anatomical landmarks (e.g. blood vessels) or the projected LED light spots, surface diagrams may be generated. The results may be plotted and compared to generated data for the eye.

More particularly, in one non-limiting configuration illustrated in FIG. 3, the lighting source 217 of each illumination devices 214, 216 may include LED arrays 300 arranged on a printed circuit board (PCB) 302. In the illustrated non-limiting example, the LED arrays 300 may include, for example, 15-30 LEDs, such as 27 LEDs. While only two illumination devices 214, 216 are illustrated in FIG. 3, it should be appreciated that more or less illumination devices 214, 216 can be utilized, such as four or more illumination devices 214, 216, or just a single illumination device 214, 216. In one non-limiting example, the PCB 302 with LED arrays 300 may be mounted onto the flat surface of the 250 mm diameter and 70 mm thick block, and focusing assembly 218 arranged along the light passage 220 may be set directly into the machined block forming the imaging unit 212.

Figure 4:
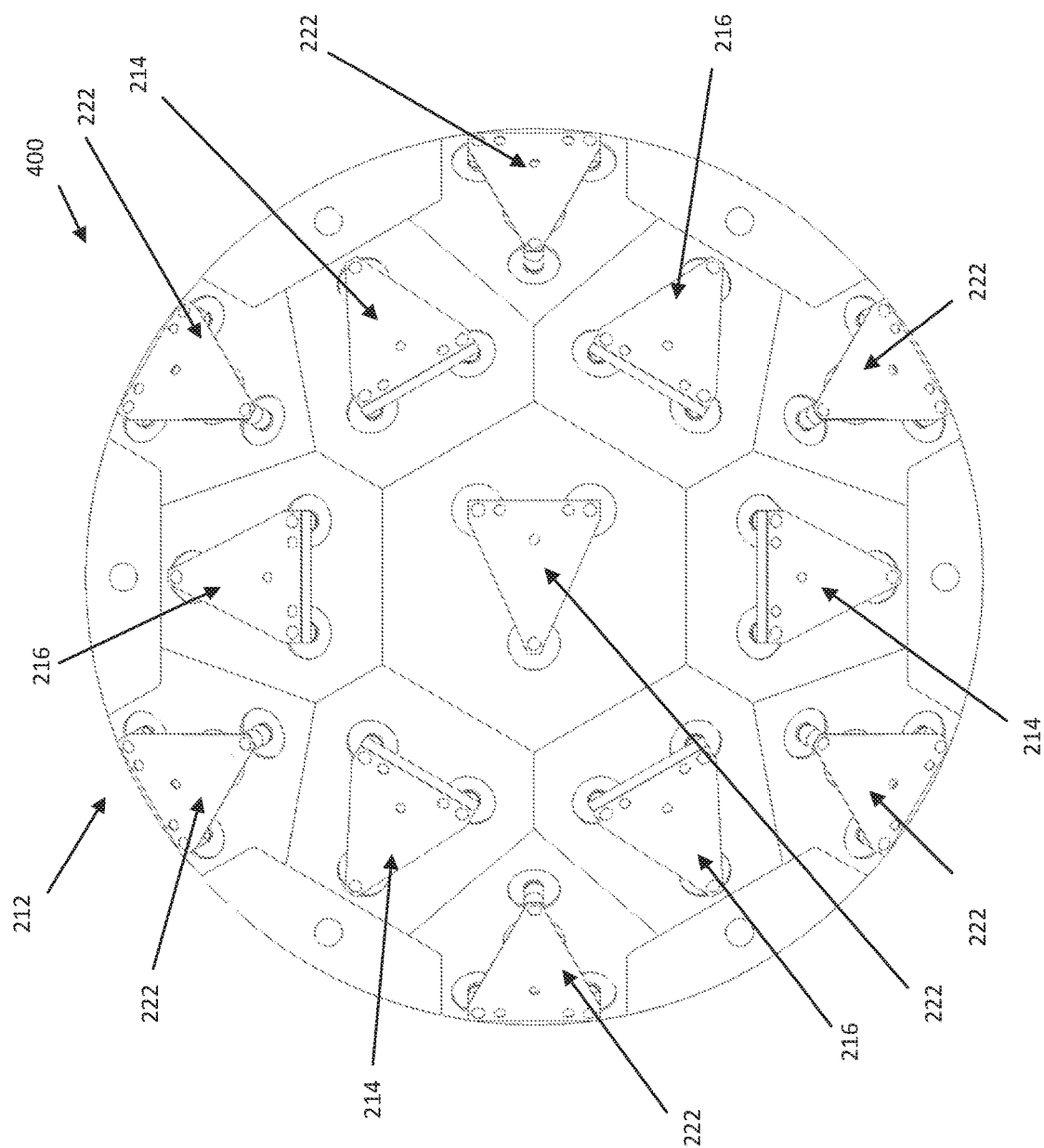
FIG. 4 is a plan view of one non-limiting example of a layout of imaging devices and illumination devices in the imaging unit of the system of FIG. 2.

More particularly, referring to FIG. 4, the above-described configuration may be expanded. In the non-limiting top illustration of an imaging unit 212, seven imaging devices 222 may be mounted on the imaging unit 212, whereby six imaging devices 222 are arranged about a periphery 400 of the imaging unit 212 and one imaging device 222 is arranged at a center 402 of the imaging unit 222. In some embodiments, a mounting standoff (not shown) is placed between the imaging unit 212 and the imaging devices 222, such that the cameras are not mounted directly onto the imaging unit 212. Pin holes may be created in the imaging unit 212 that can receive pins through the mounting standoffs to secure the mounting standoffs onto the imaging unit 212 surface. In the illustrated, non-limiting configuration, the imaging devices 222 have a polar angle of 40° and are at an azimuthal angle of 0°, 60°, 120°, 180°, 240° and 300°, plus one imaging unit 222 in the center 402, which is aligned with the z-axis (i.e. it has a polar angle of 0° and an azimuthal angle of 0°).

In the non-limiting example configuration of FIG. 4, the illumination devices 214, 216 are arranged between the imaging devices 222. The illumination device 214, 216 and imaging devices 222 may be calibrated. Hence, the positions of illumination device 214, 216 and the imaging devices 222 are known and the 3D positions of the spots may be obtained from stereo analysis between the illumination device 214, 216 and an imaging device 222 or between the images of two imaging devices 222, as will be explained. Each spot position may be measured several (for example, between three and nine) times and, assuming the surface between spots (spaced 2 mm apart), is close to spherical, the continuous surface of the eye may be obtained.

In the non-limiting example configuration of FIG. 4, six illumination devices 214, 216 are included that are mounted to the imaging unit 212 and extend through holes that are positioned at azimuthal angles of 30°, 90°, 150°, 210°, 270°, and 330° to the surface of the eye 206. Two of the six illumination devices 214, 216 may be projected onto the eye 206 at a given time and two of the six illumination devices 214, 216 may project at azimuthal angles of 30°, 90°, 150°, 210°, 270° or 330°. In one non-limiting implementation, six LED arrays may be used. Light spots may be projected onto the eye with a spot separation of, for example, 1 to 1.5 mm such that the illumination devices 214, 216 cover a spherical section of about 19 mm in diameter. Each projected spot may be imaged by two or more charge coupled device (CCD) cameras. Projections and CCD cameras may be calibrated, and hence the positions of projector and camera lenses, LED arrays, and CCDs may be known and the 3D position of the spots may be obtained from stereo analysis between the projector and a camera or between two cameras. Each spot position can be measured multiple times, for example three to nine times, and assuming the surface between spots is spherical, the surface of the eye can be obtained.

In this configuration, the illumination devices may be designed to provide a general illumination of the eye and/or to project light spots projected on to the eye 206. With this illumination, the eye 206 may be surveyed from the center out to, for example, a 22 mm sphere. To this end, in FIG. 5, the light spots may be arranged at about a generally circular pattern 504 having a diameter of 12 mm and the center of the field of view of each camera, identified as "1" through "6" can be arranged along a circular pattern 506 having a diameter of around 17 mm. As each illumination device 222 array may have, for example, 27 LEDs, the total of 162 (27 LEDS×6 illumination devices) LEDs may be projected on the 19 mm spherical section with about 1 to 1.5 mm spaced between each other.

Each projected spot may be imaged by two or more imaging devices 222 with, for example, a field of view of about 16 mm×20 mm. This non-limiting example may be with the center of the field of view of each imaging device 222 indicated with a number of "1" through "7". These dimensions are only non-limiting examples and others can be readily used, for example to accommodate different hardware configurations and/or different anatomical sizes.

Continuing with this non-limiting example, the eye 206 may be in a range of 12 to 22 mm away from the imaging device 212. At this distance, anatomical interference (e.g., the position of eye lids or, more particularly, the nose) as well as the coverage area may make it advantageous to acquire data of the eye 206 in regions or sectors, referred to herein as "swaths" to allow full coverage of the sclera. For example, the position of the nose can interfere with the ability to view all of the sclera simultaneously. Thus, for anatomical reasons, even with the eyelids pulled back, the sclera cannot be fully "spot-illuminated" and imaged at the same time.

To obtain a full survey, the sclera may be divided into three or more separate, overlapping parts. As addressed above, these parts may be referred to as "swaths." Each swath is brought to the front of the system (the pattern of spots) by having the patient rotate the eye by looking right, left-up and left-down. In one non-limiting example, each swath may be surveyed to better than 30 μm perpendicular the eye surface. In other non-limiting examples, each swath can be surveyed to better than 15 μm perpendicular the eye surface. A second independent set of swaths may optionally be obtained by having the patient look left, right-up and right-down.

Also, a light spot may direct the patient when prompted to look right, top-left, bottom-left, however the 3D position of the corresponding swaths (R-Swath, TL-Swath, BL-Swath) is not inherently known and can be difficult to measure as the eye also translates by up to 1 mm as it rotates. As such, the disclosed technique may "stitch" the three swaths together by using images of the blood vessel in the three overlapping regions of the swaths.

Figure 6A:
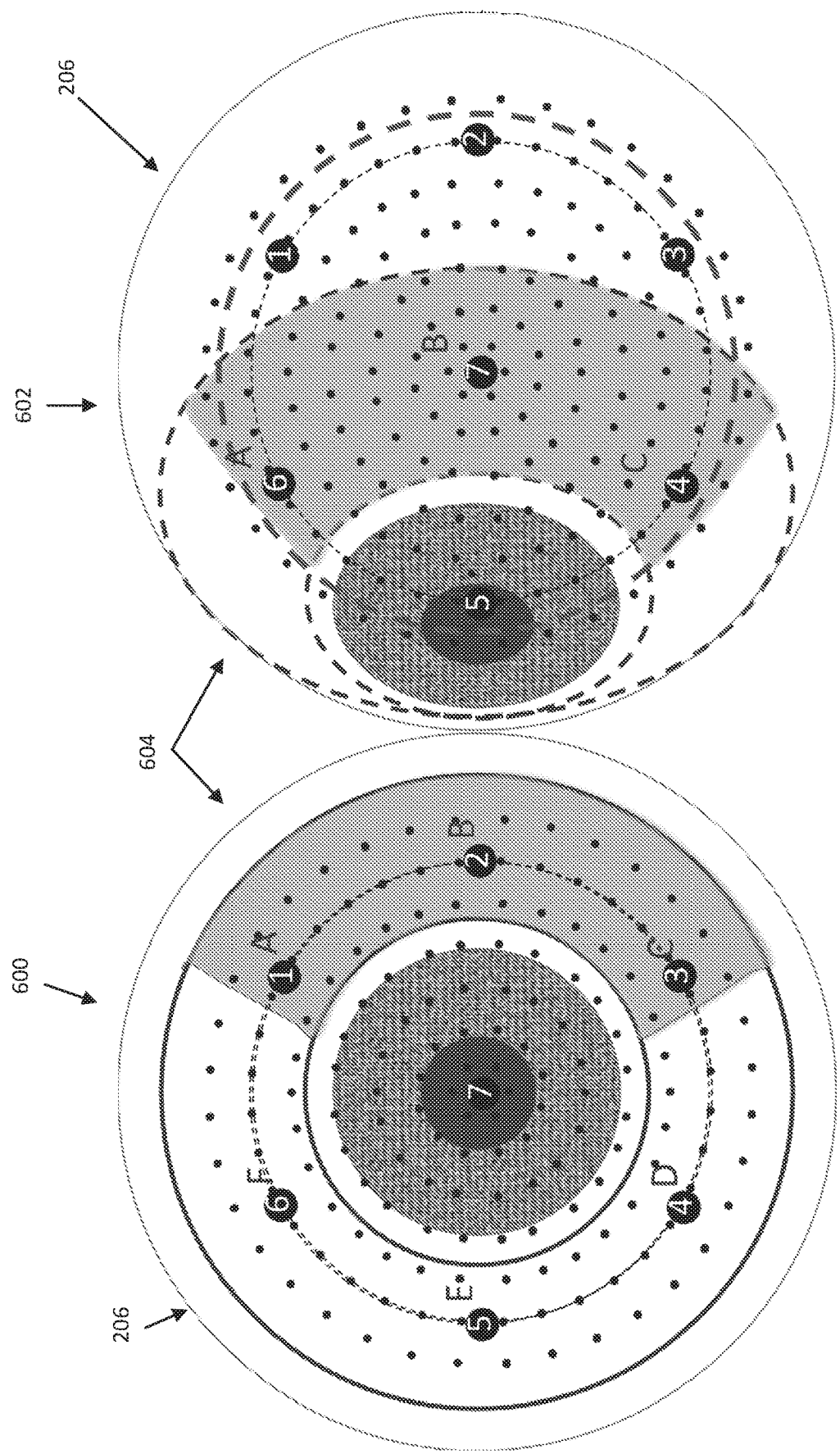
FIG. 6A is a schematic illustration of an eye in a forward and right-looking position showing illuminations, markers, and fields of view of imaging devices in accordance with the present disclosure.

As shown in FIG. 6A, one sclera is surveyed using swaths. The center of the field of view of the seven imaging devices is shown, indicated by numbers 1 to 7. The positions of the illumination devices and imaging devices axes intersect the eyeball and the spot illumination of the eye. The field of view of each of the imaging devices may be, in one non-limiting example, about 18 mm, (16 mm×20 mm), as shown in FIG. 6A for the central imaging device.

To perform a survey of the eye, including the sclera, the patient may be directed to look in a variety of directions. For example, FIG. 6A shows that movement from a forward-looking position 600 to a position 602 where the patient is looking to the right side, which allows further portions of the eye to be surveyed. In this example, when the patient looks right, a R-swath 604 moves from imaging devices 1, 2, 3 in to the field of view for imaging devices 4, 7, 6. In this case, imaging data is acquired from the eye 206, along with the light spots, by these imaging devices and partially with imaging devices 1, 3, and 5.

Referring to FIGS. 6B and 6C, the patient may be asked to sequentially look right, left-up, and left-down to image the surface of an R-swath (right) 610, LU-swath 606 (left-up) and LD-swath 608 (left-down). In some embodiments, a light spot may direct the patient when prompted to look right, left-top, and left-bottom. The sclera may also be divided into three different overlapping swaths by having the patient look left, right-up and right-down, such that the surface of each swath may surveyed. FIG. 7 shows the imaging of the left 702, right-up 704 and right-down 706 swaths.

Referring to FIGS. 5 and 6A-6C, a plurality of markers, labeled "A" through "F", may be used to correlate or "stitch" together the swathes. That is, after data for the whole eye is acquired, the swaths may be "stitched" together using the markers A-F. In the illustrated example, the six swaths (two times three) may be stitched together by using, for example, the markers A-F, which may be anatomical markers (e.g. blood vessels) or artificial markers. In the illustrated example, there are a total of six markers and each swath includes three markers. Each marker may be imaged four times including the "look-straight" position where all six markers are recorded simultaneously.

Figure 5:
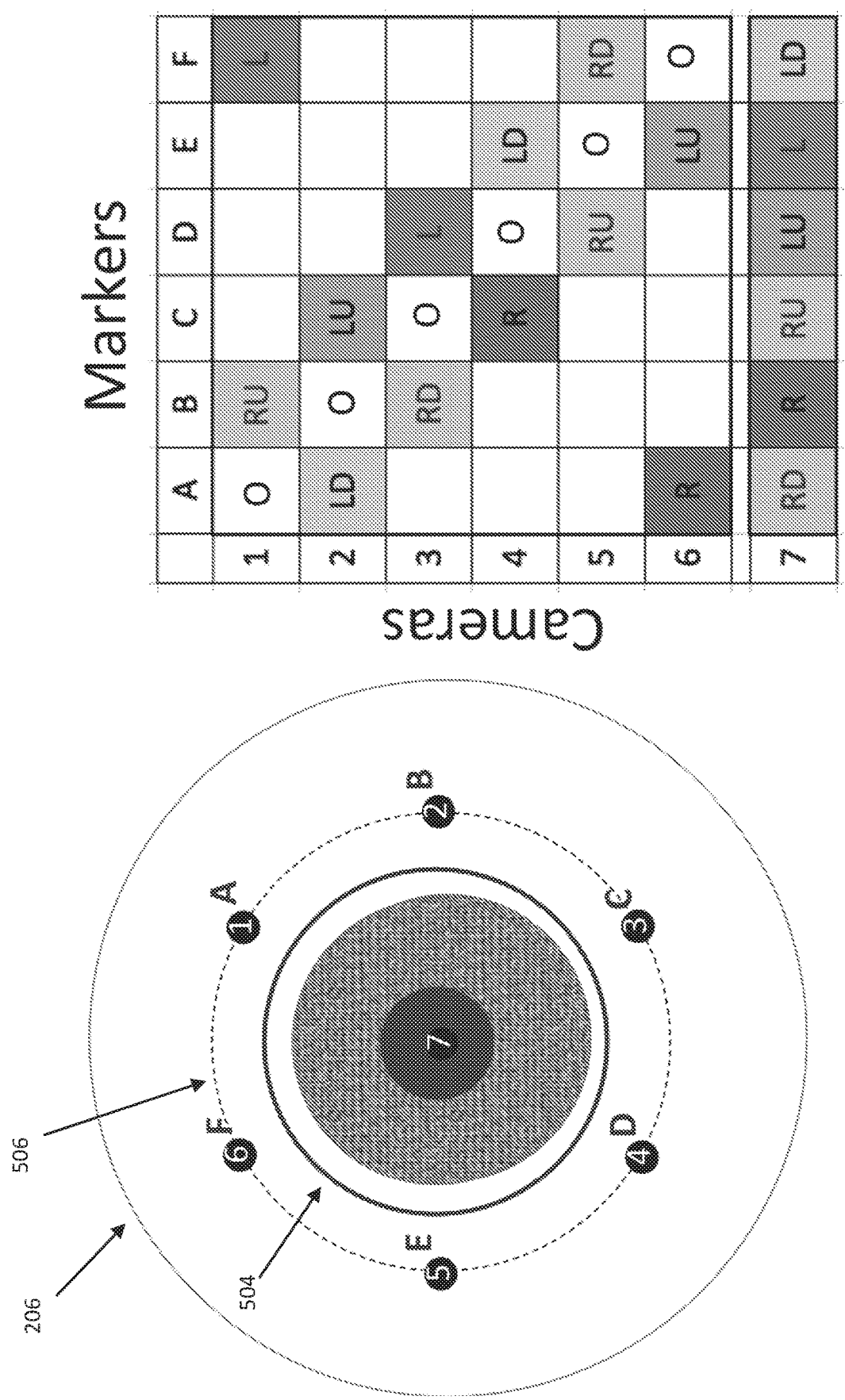
FIG. 5 is a schematic illustration of an eye showing the positions of illuminations, markers, and fields of view of imaging devices and a table of cameras versus markers in accordance with the present disclosure.

In the illustrated example of FIGS. 5 and 6C, the markers A-F are selected to be perpendicular to the axis of the imaging devices, but their positions may not be determined by stereo analysis. However, a marker A-F may be imaged at the same instant as the spots on the swath are stereo-recorded, so the 3D position of the marker A-F can be obtained from the nearby and overlapping spots.

Figure 8:
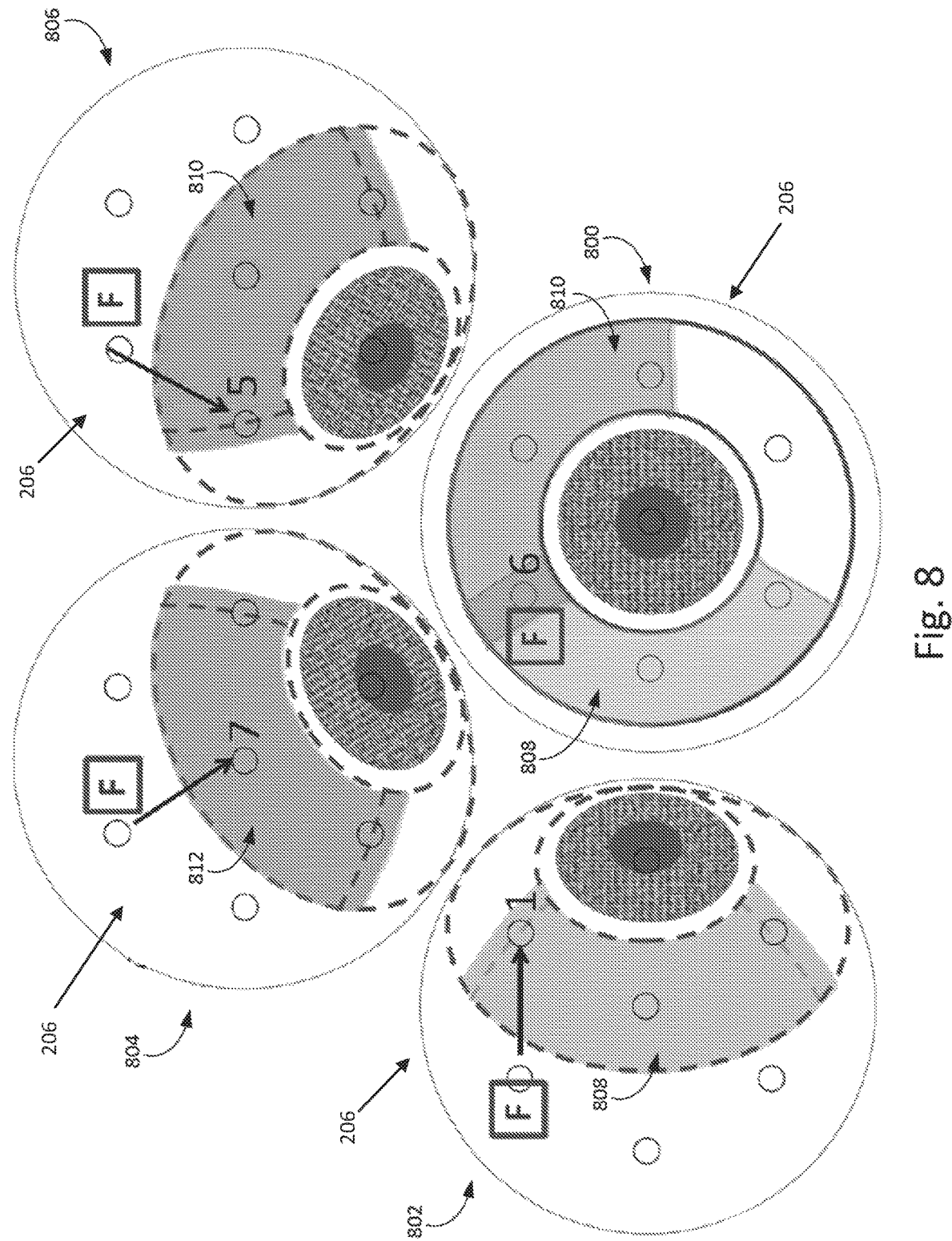
FIG. 8 is yet another schematic illustration of an eye showing the imaging of looking left-down, right-down, left and straight in accordance with the present disclosure.

Referring to FIG. 8, one non-limiting example is illustrated. In particular, the position of the F marker is shown as the eye 206 is moved through 4 positions that include "look straight" 800, "look left" 802, "look left-down" 804, and "look right-down" 806. In the look straight position 800, the F marker is located at the intersection of a first swath 808 and a second swath 810 proximate the center of the field of view of imaging device 6. As the eye moves to the look left position 802, the portion of the first swath 808 that was imaged by imaging device 6 in the look straight position 800 is now imaged by imaging device 1 and the F marker is outside the first swath 808 and proximate the center of the field of view of imaging device 6. This process continues as the eye is moved to the other positions, including the look left-down position 804, where a third swath 812 is defined. Importantly, through these four positions, marker F is imaged at least three times. First, it is imaged by imaging device 6 when the eye is in the look straight position 800 by both the first swath 808 and the second swath 810. Also, it is imaged by imaging device 5 when the eye is in the look right-down position 806, again, as part of the second swath 810.

Referring again to FIG. 5, a table is provided that shows the eye position when each of the six markers is imaged, and also shows which camera images the marker at each position. In some non-limiting examples, each marker is imaged four times during the eye mapping process. The two sets of three overlapping swaths plus the stereo analysis of the "look straight" images result in a vastly over-determined system that can then be used to perform a stitching of the swaths to obtain an accurate 3D map of the surface of the eye and, in particular, the sclera.

The above-described markers may be artificial or anatomical, as mentioned previously. In one non-limiting example, anatomical markers, such as blood vessels, are used for each of the seven eye positions, and all illumination devices may be flashed simultaneously for about 1 millisecond (ms) while images are acquired. In some examples, CCD cameras are used to capture the images. Thus, images of the blood vessels are then taken while the illumination devices flash light onto the eye for about 1 ms. Spot images and marker images may be acquired in series to accommodate the differing illumination parameters. For example, spot images may be read out in about 100 ms, then marker-images may be transferred and read out. The time between spot-images and marker images may be few ms, thus not enough time for the eye to move. In some configurations, imaging devices may be used to acquire spot and marker images simultaneously. For example, the imaging devices may include color-CCDs and the spot and marker images acquired simultaneously in different spectrums. For example, the spot-images may use the green or yellow spectrum and the marker images may use red, blue, and/or green light. In this case all images may be taken simultaneously within one or two milliseconds. It is noted that depending on the position of the eye, not all spot or marker images are of interest.

In some configurations, only images of blood vessel makers may be acquired. That is, the user of light spots may be foregone. For example, only large swaths are used to divide the eye (sclera) into a few sets of swaths (e.g., three) and use stitching software to obtain the full surface, without stereo analysis. If greater oversampling is desired, the patient may look "near right" and "far right", etc. to acquire images for 12 different directions of the eye. Alternatively, the number of imaging devices can be increased. In any case, translating the 2D positional information of camera and markers into a 1D graphing of the camera against position shows that combining the two sets of swaths can have an ambiguous solution. However, this ambiguity can be resolved by magnification of the markers. Combining three swaths provides the relative distance of the markers from the center of the eye and, hence, the shape of the eye (sclera), but not its size.

Figure 9:
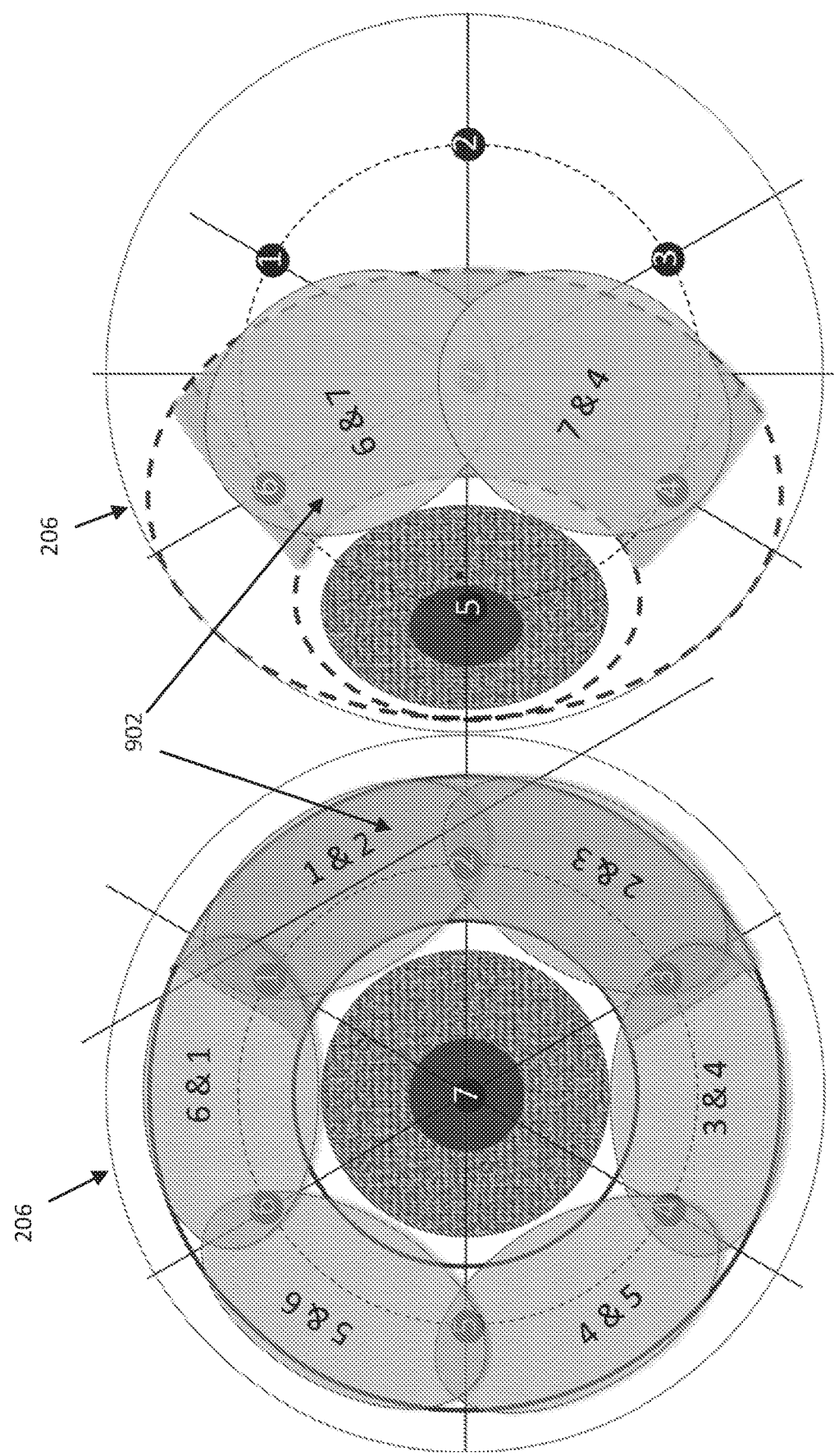
FIG. 9 is yet another schematic illustration of an eye showing stereo analysis of markers in accordance with the present disclosure.

Referring to FIG. 9, when the eye is looking straight (left example in FIG. 9), six cameras are used (except the center camera). There are six overlapping images numbered 1 through 6. Those overlapping images can be stitched together. The combined field of view of the six cameras is, when measured along the mid-line (circle through camera areas), more than twice the size of the sclera. Therefore, each point on the sclera is imaged twice and its position can be determined by stereo analysis of the two images, where the overlap area for each camera pair is available as shown in the left example of FIG. 9.

More than two images may also be combined. In addition to the small missing parts of the sclera which may be hidden behind the eye lids, there can also be a "staking" error as the images are stitched around the sclera. To survey the full sclera and to eliminate systematic and random stitching errors, the eye may, in the configurations discussed here, be divided into several swaths. FIG. 9 shows an example of the R-swath 902 on the right side. Here, several image pairs of adjacent cameras may be used to determine the 3D shape of the R-swath 902. The overlap areas 6 & 7 and 7 & 4 are shown, but stereo analyses of the other pairs such as images from cameras 1, 2, 3, 5 partially overlapping with 6, 7, or 4 may also result in 3D images of parts of the R-swath 902. A best-fit algorithm may be used to combine these images to obtain the absolute shape and dimensions of the swath. All six swaths may be measured this way, but their six coordinates in space may not be known. However, the sclera can be divided into two sets of three overlapping swaths and can be, together with the complete shape from the "look straight" position, combined into a single shape.

Combining one set of three swaths may have a higher precision and accuracy as the three swaths can be stitched together using the images of the overlap areas from the cameras with their axes perpendicular the sclera (camera 6 and 4 for the R-swath), as it is described above.

It should be pointed out that in all seven eye positions all cameras may take images simultaneously using exposures of a few milliseconds. All seven images can be read out in less time than it takes the eye to move to a new position.

By layering both the above-analysis and stereo analysis, size can be readily discerned. Again, the stereo analysis can utilize light spots or can use anatomical markers such as blood-vessels. For stereo analysis of markers, the possible regions to be imaged by two cameras (taken at ±20°) are shown in FIG. 9. To find the 3D position of the marker area, the distortions are considered in the stereo analysis. It is possible to use additional camera pairs for the stereo analysis of the R-Swath (e.g. 1 and 6, 1 and 7, perhaps more). Where the R-Swath serves as an example for all swaths.

Figure 10:
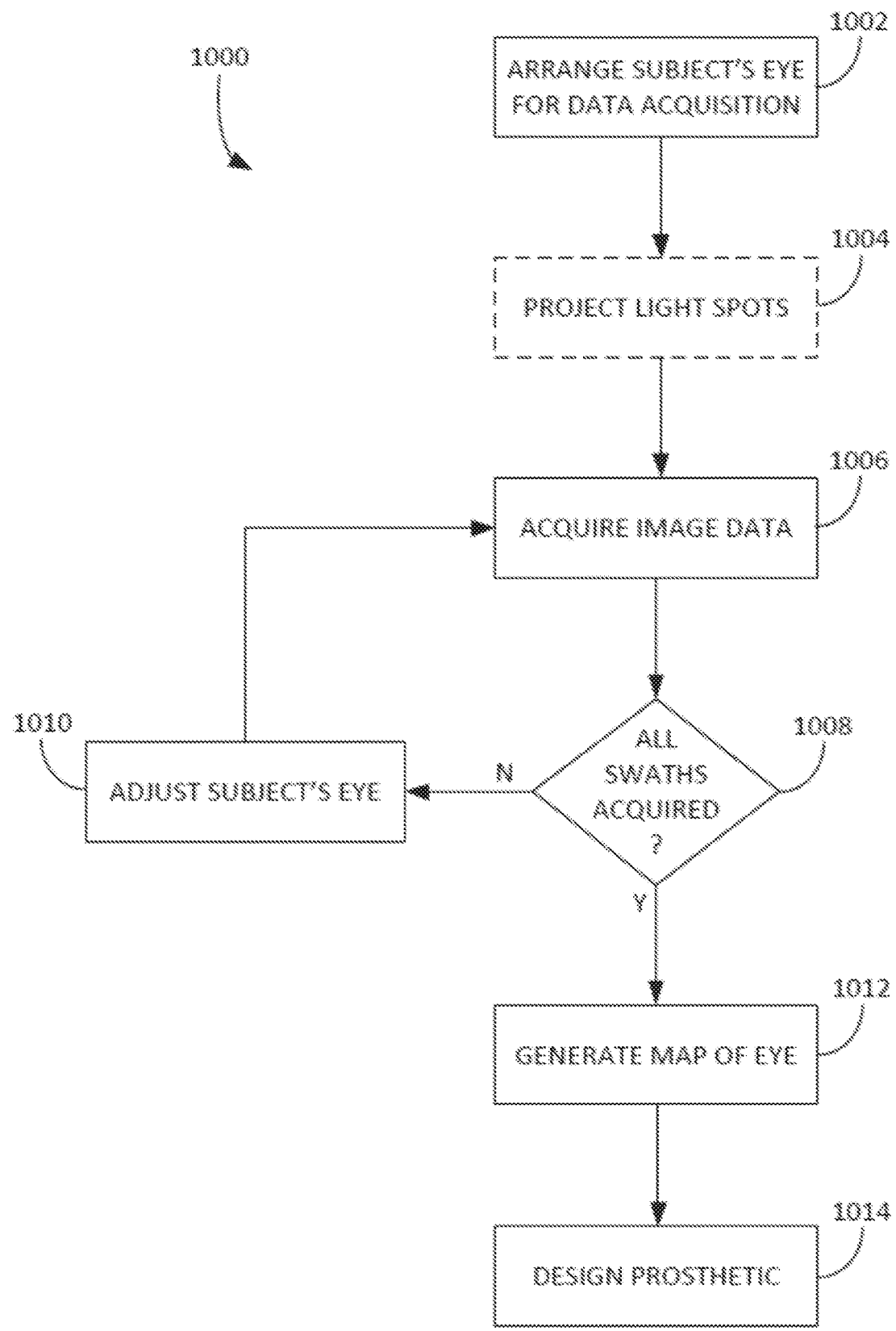
FIG. 10 is flow chart setting forth steps of a method for determining a profile of an exterior or creating a three-dimensional map of an eye and creating a lens using the profile or map in accordance with the present disclosure.

Referring to FIG. 10, one example of a method 1000 in accordance with the above-described systems and methods begins at process block 1002 by arranging a subject to have data acquired from an eye. For example, a subject can be situated within a patient-engagement frame 204 of the system 200 described above with reference to FIG. 2. At process block 1004, light spots are optionally projected onto the eye using illumination sources, such as illumination devices 214, 216 described above. In some embodiments, six illumination devices 214, 216 may be used. With the eye illuminated, image data is acquired at process block 1006. As described, the acquisition of image data at process block 1006 may include multiple sequential acquisitions and/or simultaneous acquisitions, and may include one or more imaging devices 222, such as CCD cameras. In some embodiments, seven cameras are used to obtain images of the eye, which can be taken as the eye is in several different orientations.

At decision block 1008, a check is made to determine if all desired swaths have been acquired. If not, the subject's eye position is adjusted at process block 1010 and the imaging process is repeated. This continues until all swaths are acquired. Thereafter, a 3D map of the eye and, more particularly, the sclera, is generated at process block 1012. Based on this map produced at process block 1012, a prosthetic may be designed at process block 1014, which does not rely on trial and error or repeated re-fittings. The prosthetic may be a prosthetic lens that fits over a cornea of the eye to engage the sclera and form a fluid pocket between the prosthetic lens that surrounds the cornea.

To provide the accuracy desired, at setup and/or before performing the process described above with respect to FIG. 10, the positions of all imaging devices and illumination devices can be coordinated and calibrated. That is, the system can be used to measure the position of the imaging devices and illumination devices relative to the system and/or each other.

Figure 11:
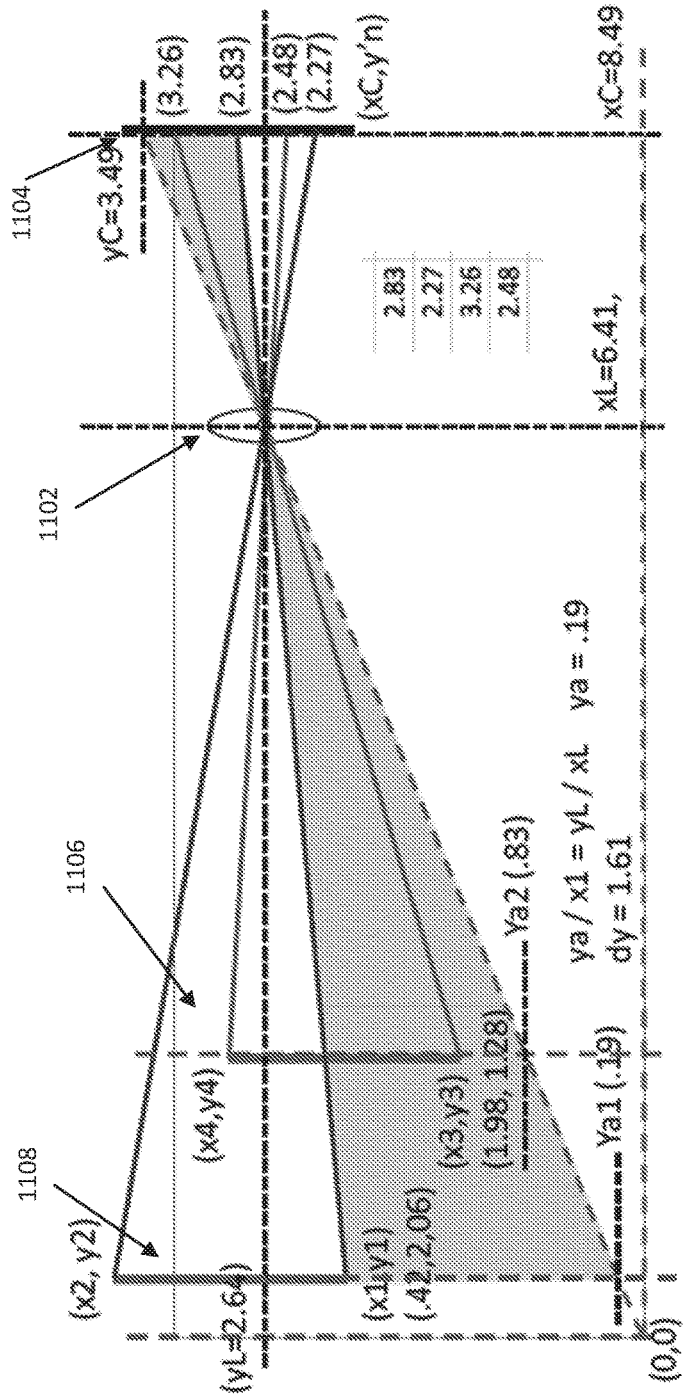
FIG. 11 shows an extended object of known size that is viewed in two known positions that can be used to calibrate the system of FIG. 2.

The positions of all cameras and projectors are preferably known in the coordinate system of the disclosed Sclervey device. This may require measuring the position of all lenses 1102 plus the positions of all CCDs and LED arrays. FIG. 11 shows an extended object of known size that is viewed in two known positions 1106, 1108 and the equations shown are solved for the position of the lens 1102 (xL, yL) and of the CCD (xC, yC). The two-dimensional (2D) method shown in FIG. 11 may easily be expanded to three-dimensional (3D) applications, such as that performed by the Sclervey device.

Figure 12:
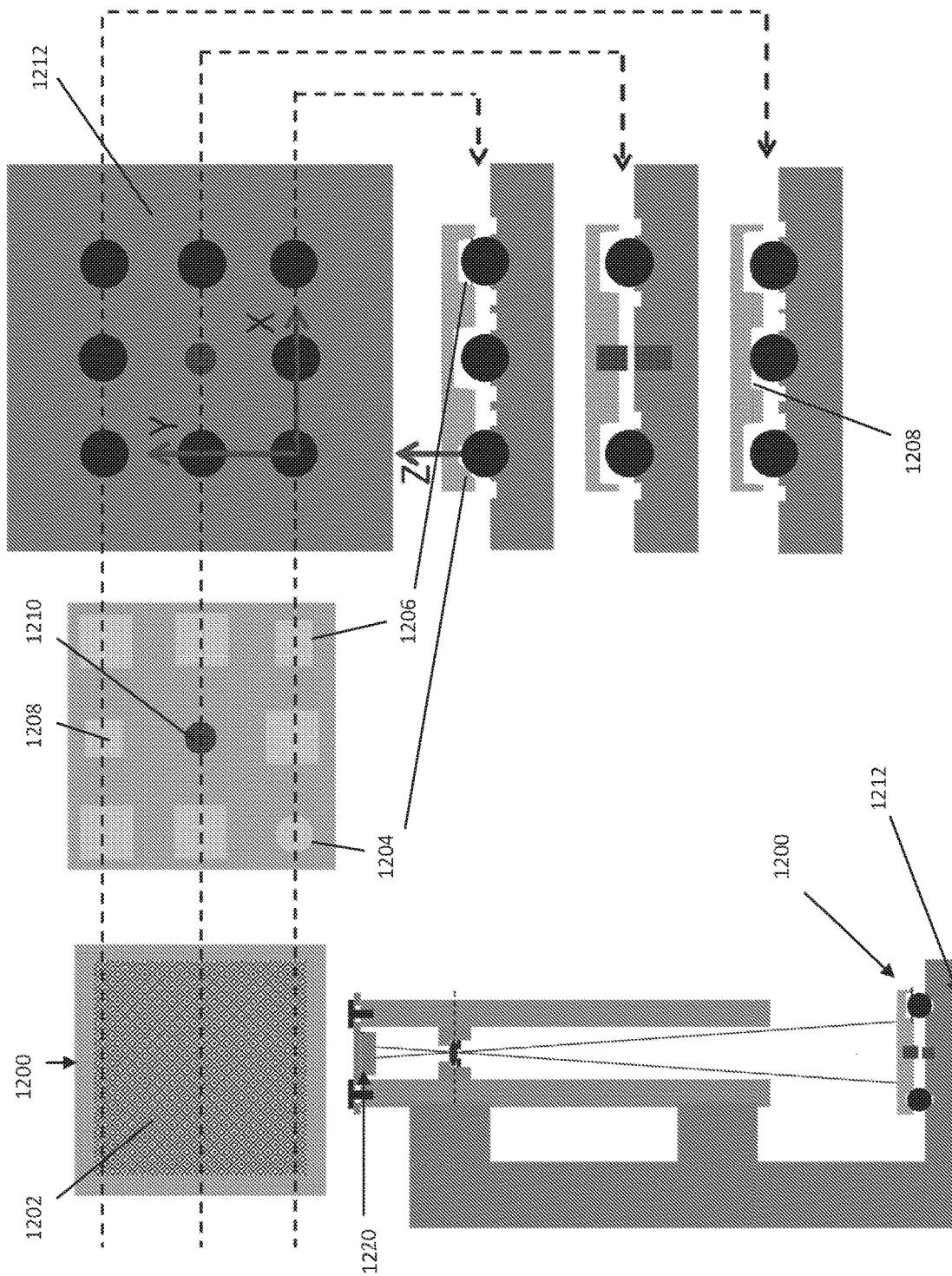
FIG. 12 is a schematic illustration of a calibration process in accordance with the present disclosure.

Referring to FIG. 12, a method of calibration can be performed that uses coded masks 1202, checker boards with some fields switched to give the binary position of rows and columns, and bench size CMMs (computer measuring machines). Both can be successfully used by ATLAS/LHC/CERN to a sub-micron precision. The coded masks 1202 are the objects viewed by the imaging devices and the CMM gives the position of the masks by measuring spheres.

The calibration object 1200 has a mask 1202 mounted on its top side and sits kinematically on three spheres using a cone 1204, slot 1206, and pad 1208. A magnet 1210 holds it in position. The calibration object 1200 can be rotated 180° by using the three other ball positions, and the balls are also held in position by magnets. The balls on the base and the mask surface on top of the calibration object 1200 are measured with the CMM in the 0° and 180° position and the 3D mask position with respect to the three balls is obtained from the camera images.

As shown in FIG. 12, the mask 1202, usually printed onto glass, is placed onto an aluminum plate, which sits kinematically (cone: X, Y, Z, slot: X×Y and Z×X, pad: Y×Z) on three balls. This calibration object 1200 can be rotated 180° around the Y-axis by setting it onto a second set of balls. A CMM may be used to measure the surface of the mask 1202 (Z) and the positions (X, Y, Z) of the eight balls glued to the base 1212. The calibration object 1200 is pulled onto the three balls by a magnet 1210, (latter is important when the calibration object 1200 sits at an angle, see below). The calibration object 1200 is imaged by a CCD camera 1220 in the 0° and 180° positions and the X-Y position of the mask 1202 is determined from the X and Y shifts of the mask image. For redundancy the calibration object 1200 is also imaged in the 90° and 270° position. Hence the position of the mask 1202 with respect to the three balls is known. This method is successfully used by ATLAS/LHC/CERN at a precision of microns.

Figure 13:
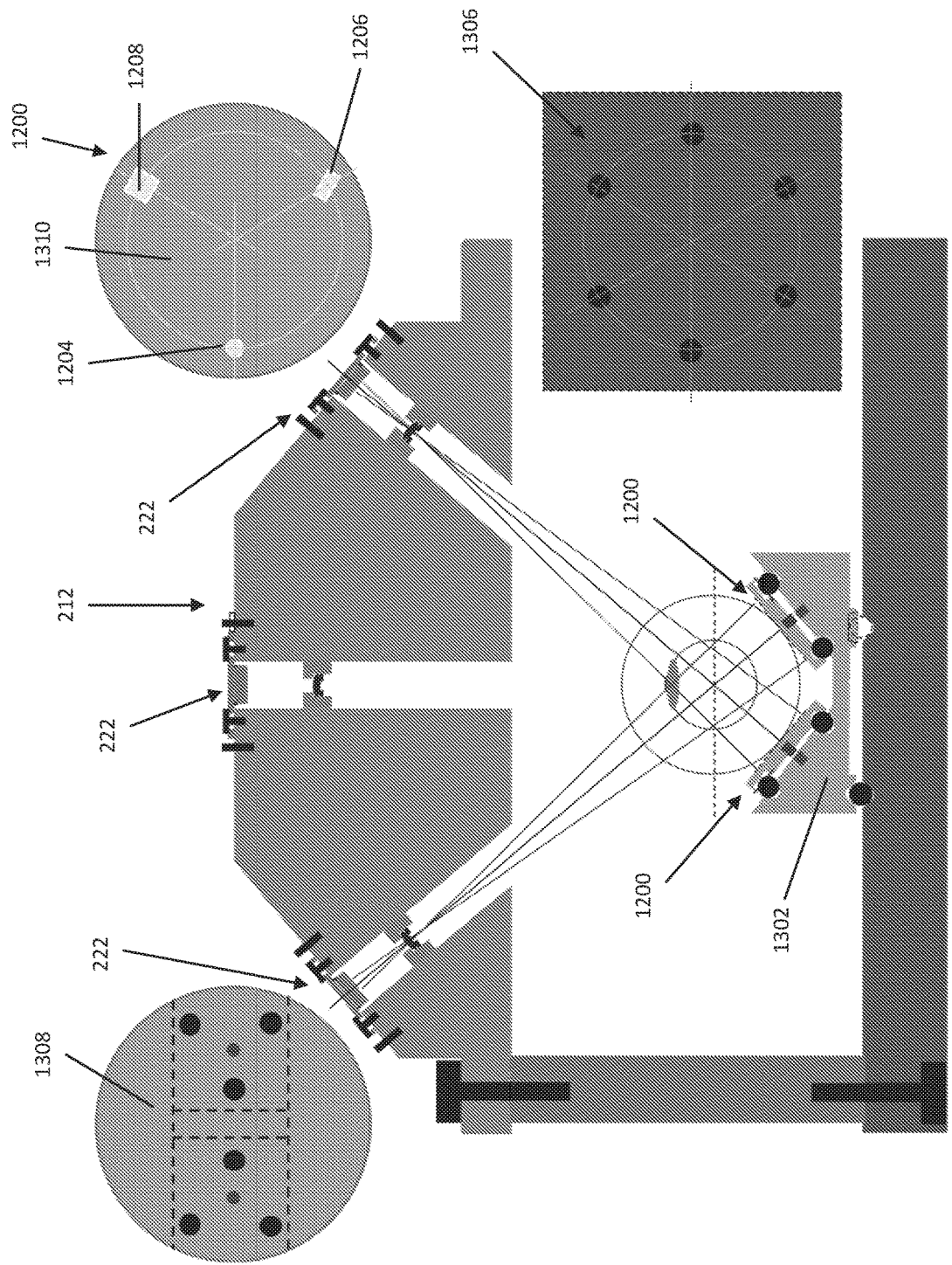
FIG. 13 shows the "Lower Cradle" with two calibration objects mounted onto the two surveyed triplets.

FIG. 13 shows the "Lower Cradle" 1302 with two calibration objects 1200 mounted onto the two surveyed triplets. The Cradle 1302 itself sits kinematically on three of the six balls glued into the base 1306. The balls are surveyed. The cradle 1302 can be set down into six positions each time for presenting masks (e.g. masks 1202) in known positions to two of the azimuthal cameras 222. As shown in FIG. 13, the Sclervey Calibration stand shows six balls glued into the base 1306, and the Lower Cradle 1302 includes from-top 1308 and from-bottom view 1310, and two calibration objects 1200.

Figure 14:
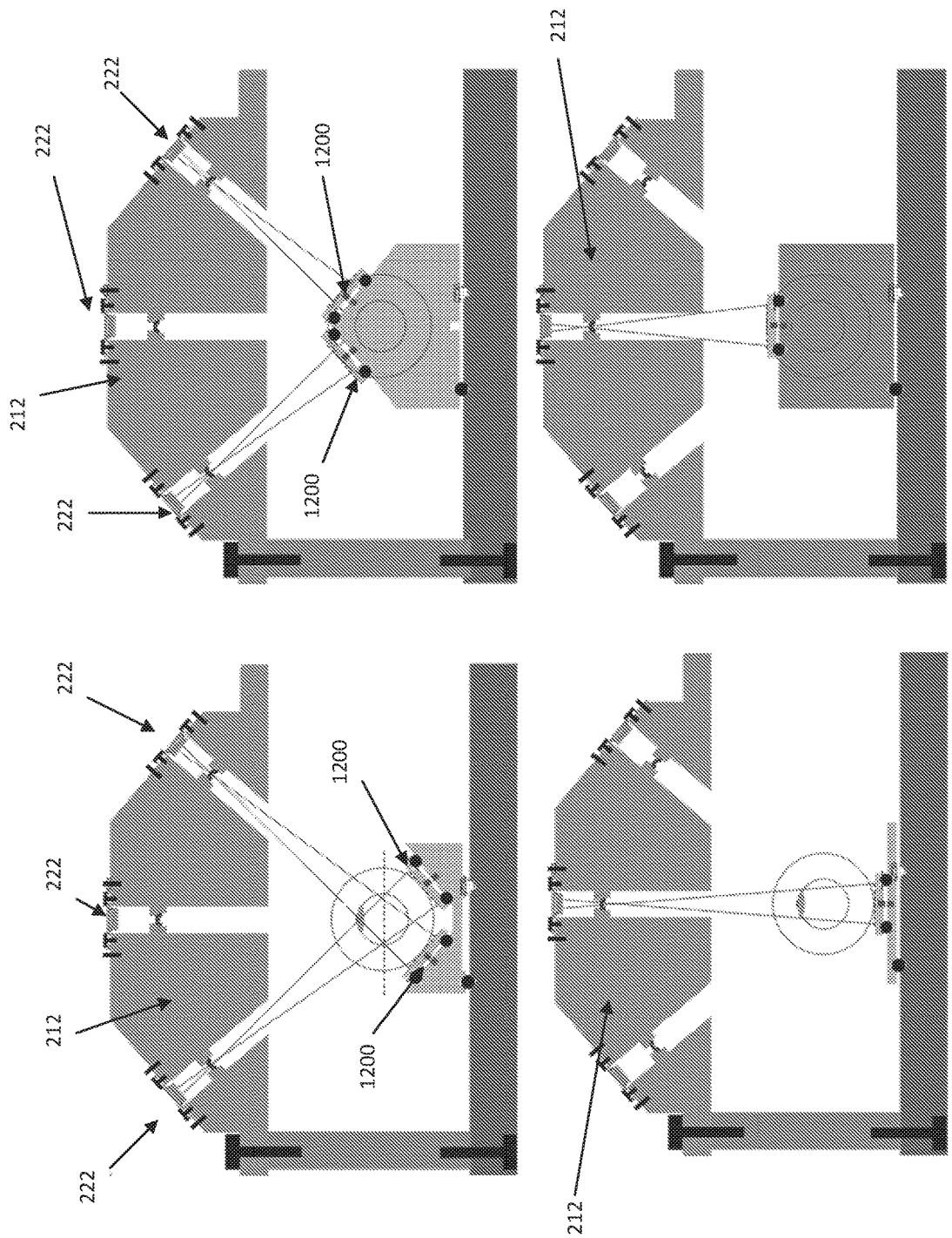
FIG. 14 shows the calibration of all cameras.

FIG. 14 shows the calibration of all cameras 222 of an imaging unit 212. Each camera 222 will image two calibration objects 1200 in two known positions. The procedure is redundant as three positions of the cradle would be sufficient. As shown in FIG. 14, top-left and top-right show the calibration objects 1200 in the two positions needed for calibrating the azimuthal cameras. Bottom-left and bottom-right show the same for the center camera.

FIG. 15 shows the calibration of the projectors where the spots are projected onto two calibrated planes at different distances from the projectors. These spots are imaged by several calibrated cameras. Their positions are determined by stereo analysis of two or more image-pairs. The positions of the lower-screen and upper-screen spots define the vector for each LED projected. The block can be set into six positions, where only three are needed, resulting in a redundant set of measurements. Further, the stereo analysis of the spots results in the (X, Y, Z) position of each spot, whereas the spot is known to be on the surface of the lower or upper screen. This permits a user to check the consistency of the camera and projector calibration. As shown in FIG. 15, lower and upper calibrated screens are provided to project all LEDs at two distances from the projector lenses.

As such, as illustrated above, the absolute scale can be obtained by stereo analysis either of the LED spots or blood vessels, should anatomical markers be used. With all cameras calibrated, the stereo analysis gives the LED-spot or the blood vessel (both on the surface of the sclera) in the coordinate system of the multi-camera-device. The position of the eye, hence the swath, is not known and the stitching procedure is needed to combine all the swaths into the complete sclera.

In some non-limiting examples, the stereo-images (LED-spots or blood-vessels) obtained in the look-straight position may comprise the full eye and stitching may not be needed. However, some parts of the swaths may not imaged by the cameras. Sometimes, data from the Sclervey shows that the six individual swaths can be stitched directly to the incomplete, "look-straight" map to obtain the full sclera.

EXAMPLES

In one experimental example of the above-described systems and methods, an LED light was projected on to a 25 mm diameter PVC-sphere which may be moved over a range of ±6 mm in steps of 1 mm (13×13=169 positions) and the spot was monitored by two cameras. A white plastic hemisphere and two cameras at polar angles of ±30° were used, and a swath of 12 mm×12 mm was surveyed. In place of using an array, a spot from a single LED that may be moved about the hemisphere in 1 mm steps over the surface was used. The plastic model of the eye was then mapped to a 12 mm×12 mm surface of the eye to about 50 µm by using a single LED and moving the image over the sphere in steps of 1 mm. In order to set up the test, a projector LED array with nine projects was placed on one PCB. The PCB was mounted on a PCB support structure with projector lens. The two cameras were able to produce the PVC sphere in a translation stage with 3D mapping (x, y, z) in a range of +12 mm.

Figure 16B:
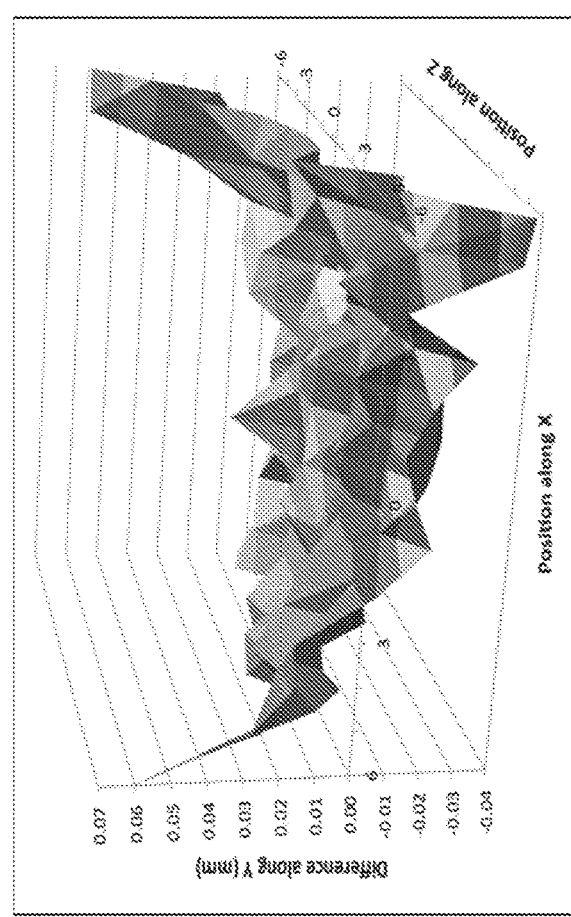
FIG. 16B illustrates the error of measurement by showing the difference between the sphere and the surveyed surface.
Figure 16A:
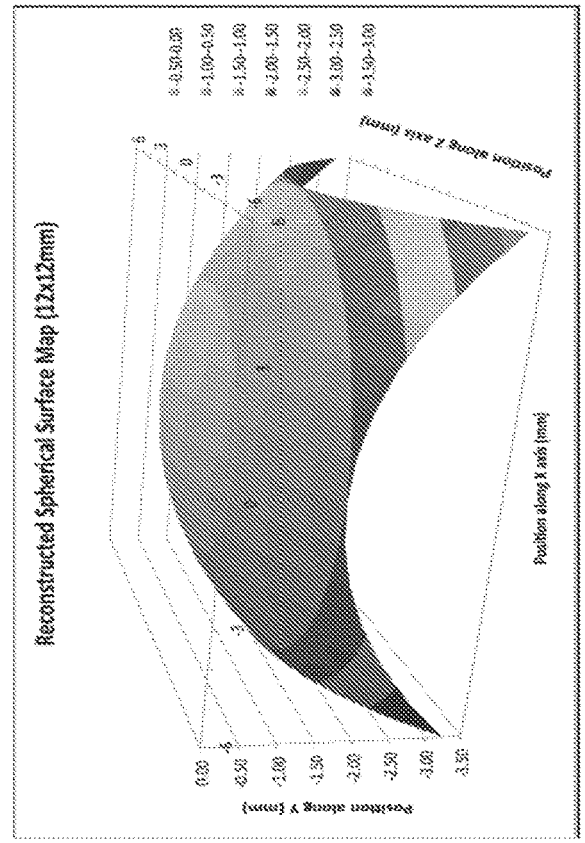
FIG. 16A shows a mapped contour of the surveyed 12 mm×12 mm essentially perfect surface of a sphere.

FIG. 16A shows a mapped contour of the surveyed 12×12 mm spherical surface of the eye. FIG. 16B illustrates the error of measurement by showing the difference between the sphere and the surveyed surface. In FIG. 16B, the difference between the (essentially) perfect sphere and the surveyed surface has a standard deviation of 19 µm.

To fit a scleral lens, it can be sufficient to know the shape of the sclera to about 100 to 200 µm. As shown above, each swath surveyed may be about 20 µm perpendicular the eye surface, which is ten times better than needed. However, the positions of the swaths with respect to the other swaths may not be known. Using the pupil, the eye is looking into a camera in each of the seven positions, which may not be sufficient as eyes are known to translate in and out as well as laterally when they rotate.

Figure 17B:
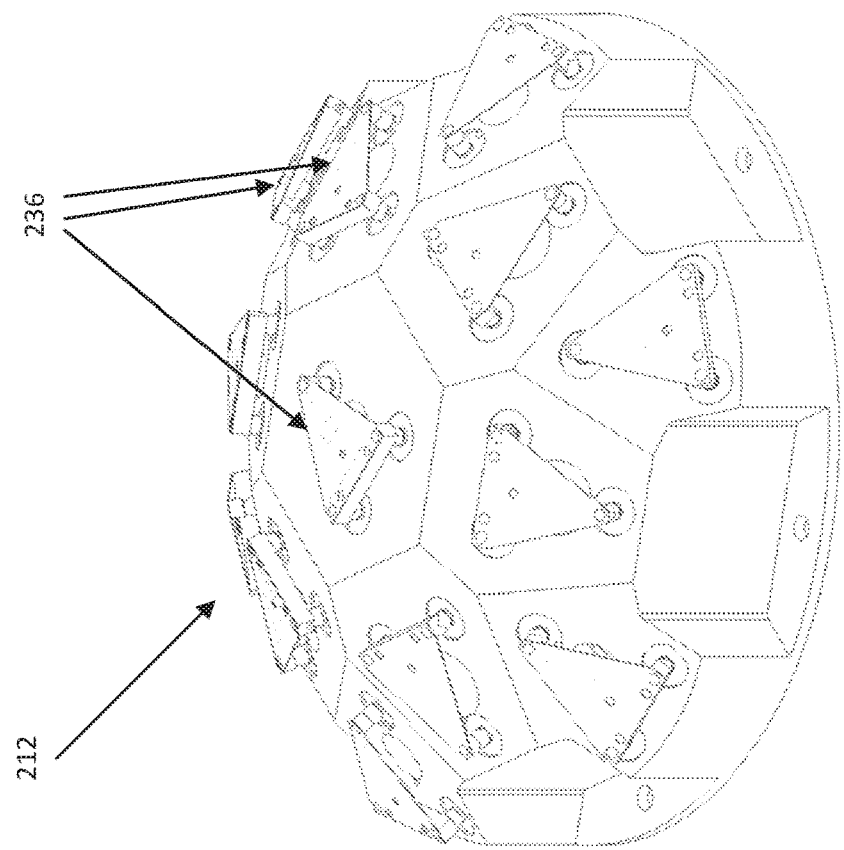
FIG. 17B is a perspective view of the imaging unit body with illumination devices and imaging devices installed.
Figure 17A:
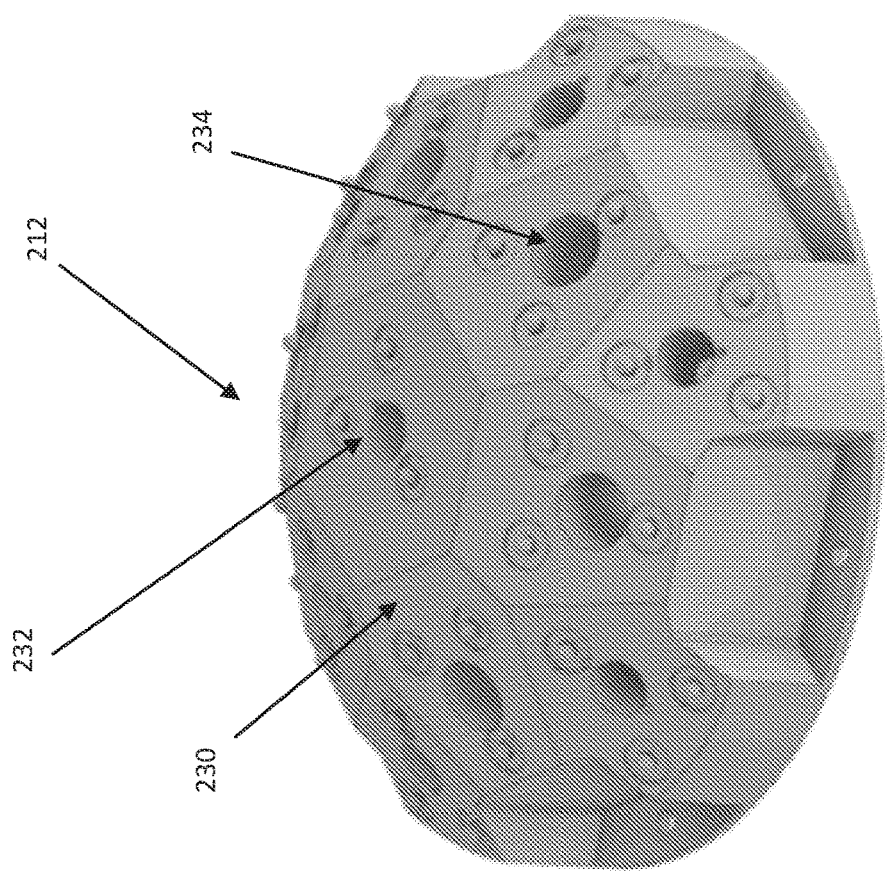
FIG. 17A is a perspective view of the imaging unit body without illumination devices or imaging devices installed.

Referring now to FIGS. 17A and 17B, a perspective view of the imaging unit 212 is shown. As can be seen in the figures provided, the imaging unit 212 can comprise a body 230 that is formed of one single continuous piece. In some non-limiting examples, the body 230 of the imaging unit 212 is an injection molded component. In other embodiments, the body 230 can be 3D printed to form the shape shown in the figures. In still other embodiments, the body 230 is cast and then machined to have the flat surfaces shown.

The body 230 of the imaging unit can be provided with a plurality of first apertures 232 and a plurality of second apertures 234 extending through the body, which are sized to accommodate illumination devices 214, 216 and imaging devices 222. For example, first apertures 232 may be positioned to accommodate imaging devices 222, while second apertures 234 may be configured to receive illumination devices 214, 216. In some non-limiting examples, first apertures 232 have a smaller diameter than second apertures 234. However, it should be appreciated that other shapes and sizes can be used to accommodate illumination devices 214, 216 and imaging devices 222, such that the disclosed shapes and sizes should not be considered limiting. For example, in some embodiments, elongated slots are positioned about the body 230 and are sized to accommodate both illumination devices 214, 216 and imaging devices 222. In some embodiments, the illumination devices 214, 216 and imaging devices are not mounted directly to the body 230 of the imaging unit 212. Instead, these components may be mounted to a mounting standoff 236, which can be used to accurately locate the devices while decreasing the manufacturing costs of the overall system 200.

Referring to FIG. 18, an example of the internal structure of the imaging unit 212 is shown and described. In some non-limiting examples, light passages 220 and imaging passages 228 are formed integrally within the body 230 of the imaging unit 212. In some non-limiting examples, the light passages 220 and imaging passages 228 may be machined into the body 230, which may be cast, molded, or otherwise formed (i.e. machined on a 5-axis machine) to have the proper surface finishes, shape, and features shown. Focusing assemblies 218 may be positioned within the light passages 220 after forming the component, and optional optics 226 may be positioned within the imaging passage 228 after the body 230 has been formed. In some non-limiting examples, the body 230 is cast or otherwise molded to provide a number of passages that are aligned and configured to accommodate illumination devices 214, 216 and imaging devices 222. Illumination devices 214, 216 and imaging devices 222 may be coupled to inserts that are configured to extend through the passages created in the body 230 of the imaging unit 212 and fit securely within the passage. In some embodiments, the focusing assemblies 218 or optional optics 226 may be coupled to the inserts, which may internally define a light passage 220 or imaging passage 228. Fasteners can be used to mount the illumination devices 214, 216 and imaging devices 222 into position over the light passages 220 and imaging passages 228, such that the unit can then be calibrated. As discussed with respect to FIG. 17B, mounting standoffs 236 may also be used to couple the illumination devices 214, 216 and imaging devices 222 into the proper position over the necessary passages formed in the body 230 of the imaging unit 212.

Illustrative examples of the technologies disclosed herein were provided above for purposes of enabling one skilled in the art to practice the contents of the disclosure. While many examples were provided, it should be appreciated that these examples and illustrations have been provided only as examples and should not be considered limiting in any way. An embodiment of the technologies may include any one or more, and any combination of, the examples described above.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for mapping an exterior surface of an eye of a subject comprising:
   a support structure configured to engage the subject and position an eye of the subject in a predetermined position;
   at least two illumination sources configured to direct light on to the eye of the subject in the predetermined position;
   a plurality of imaging devices separated from and directed toward the support structure to acquire image data of the eye of the subject when the light is positioned thereon; and
   a processor configured to receive the image data of the eye of the subject from the plurality of imaging devices and generate a three-dimensional map of the eye, including a sclera, from the image data.

2. The system of claim 1, wherein the processor is configured to illustrate the three-dimensional map of the sclera of the eye and design a lens for the eye based on the three-dimensional map.

3. The system of claim 1, wherein the processor is configured to design, using the three-dimensional map of the eye, a lens that fits over a cornea of the eye to engage the sclera and form a fluid pocket between the lens that surrounds the cornea.

4. The system of claim 1, wherein the system comprises six illumination sources, and each illumination source comprises multiple light emitting diodes (LEDs).

5. The system of claim 4, wherein the multiple LEDs are configured to project light spots onto the eye and wherein the processor is configured to perform a stereo analysis of the image data using the light spots.

6. The system of claim 4, wherein the six illumination sources are projected to the eye at angles of 30°, 90°, 150°, 210°, 270°, 330° respectively.

7. The system of claim 1, wherein the plurality of imaging devices comprise seven cameras, and six cameras are arranged to position to the eye at angles of 0°, 60°, 120°, 180°, 240°, 300° respectively and one camera is positioned upon a central axis of the eye.

8. The system of claim 1, wherein the three-dimensional map of the sclera of the eye is divided into multiple swaths, and each swath is obtained when the eye is rotated to a predetermined position.

9. The system of claim 8, wherein the processor is configured to determine one of the multiple swaths when the eye looks right.

10. The system of claim 8, wherein the processor is configured to stitch the multiple swaths together to form a complete three-dimensional map of the sclera of the eye using markers.

11. A method for generating lens for an eye of a subject comprising:
    arranging an eye of a subject at a distance from a plurality of illumination sources and a plurality of imaging devices;
    projecting light onto the eye of the subject using the illumination sources;
    acquiring image data of the eye of the subject and the light using the plurality of imaging devices;
    generating a three-dimensional map of the eye, including the sclera, using the image data; and
    designing, using the three-dimensional map of the eye, a lens that fits over a cornea of the eye to engage the sclera and form a fluid pocket between the lens that surrounds the cornea.

12. The method of claim 11, further comprising illustrating the three-dimensional map of the sclera of the eye and a design for the lens for the eye based on the three-dimensional map.

13. The method of claim 11, further comprising designing, using the three-dimensional map of the eye, a prosthetic lens that fits over a cornea of the eye to engage the sclera and form a fluid pocket between the prosthetic lens that surrounds the cornea.

14. The method of claim 11, wherein the system comprises six illumination sources, and each illumination source comprises multiple light emitting diodes (LEDs).

15. The method of claim 14, wherein each illumination source comprises a number of LEDs in a range of 15 to 30 LEDs.

16. The method of claim 14, wherein the six illumination sources are projected on to the eye at angles of 30°, 90°, 150°, 210°, 270°, 330° respectively.

17. The method of claim 11, wherein the plurality of imaging devices comprise seven cameras, and six cameras are arranged about the eye at angles of 0°, 60°, 120°, 180°, 240°, and 300° respectively and one camera is positioned upon a central axis of the eye.

18. The method of claim 11, wherein the three dimensional map of the sclera of the eye is divided into multiple swaths, and each swath is obtained when the eye is rotated to a predetermined position.

19. The method of claim 18, further comprising stitching the multiple swaths together to form a complete three-dimensional map of the sclera of the eye.

20. A method for surveying sclera of an eye comprising:
    arranging an eye at a distance from a plurality of imaging devices;
    acquiring image data of the sclera of the eye using the plurality of imaging devices, wherein each point on the sclera is imaged at least twice;
    dividing the sclera of the eye into multiple overlapping swaths;
    determining a three-dimensional shape for each of the multiple overlapping swaths by using the acquired image data comprising at least two images for each point;
    combining the multiple overlapping swaths to form a three-dimensional map of the sclera of the eye using the image data for overlap areas of the multiple swaths; and
    designing, using the three-dimensional map of the sclera of the eye, a lens that fits over a cornea of the eye to engage the sclera and form a fluid pocket between the lens that surrounds the cornea.

* * * * *